United States Patent
Kong et al.

(10) Patent No.: US 7,282,328 B2
(45) Date of Patent: Oct. 16, 2007

(54) HELICASE DEPENDENT AMPLIFICATION OF NUCLEIC ACIDS

(75) Inventors: Huimin Kong, Wenham, MA (US); Myriam Vincent, Cambridge, MA (US); Yan Xu, Beverly, MA (US)

(73) Assignee: New England Biolabs, Inc., Ipswich, MA (US)

( * ) Notice: Subject to any disclaimer, the term of this patent is extended or adjusted under 35 U.S.C. 154(b) by 551 days.

(21) Appl. No.: 10/665,633

(22) Filed: Sep. 19, 2003

(65) Prior Publication Data

US 2004/0058378 A1    Mar. 25, 2004

Related U.S. Application Data

(60) Provisional application No. 60/412,298, filed on Sep. 20, 2002, provisional application No. 60/446,662, filed on Feb. 11, 2003.

(51) Int. Cl.
*C12Q 1/68* (2006.01)
*C12P 19/34* (2006.01)
*C07H 21/02* (2006.01)
*C07H 21/04* (2006.01)

(52) U.S. Cl. .................. 435/6; 435/91.2; 536/23.1; 536/24.3

(58) Field of Classification Search ............... None
See application file for complete search history.

(56) References Cited

U.S. PATENT DOCUMENTS

| | | |
|---|---|---|
| 4,683,195 A | 7/1987 | Mullis et al. |
| 4,683,202 A | 7/1987 | Mullis |
| 4,800,159 A | 1/1989 | Mullis et al. |
| 5,176,995 A * | 1/1993 | Sninsky et al. ............ 435/6 |
| 5,455,166 A | 10/1995 | Walker et al. |
| 5,470,723 A | 11/1995 | Walker et al. |
| 5,494,810 A | 2/1996 | Barany et al. |
| 5,714,320 A | 2/1998 | Kool |
| 5,716,819 A | 2/1998 | Chatterjee |
| 6,214,587 B1 | 4/2001 | Dattagupta et al. |
| 6,235,502 B1 | 5/2001 | Weissman et al. |
| 6,306,588 B1 | 10/2001 | Solus et al. |
| 6,555,349 B1 | 4/2003 | O'Donnell |
| 6,977,148 B2 * | 12/2005 | Dean et al. ............ 435/6 |
| 2001/0018182 A1 | 8/2001 | Friend |
| 2003/0219792 A1* | 11/2003 | Armes et al. ............ 435/6 |

FOREIGN PATENT DOCUMENTS

| | | |
|---|---|---|
| JP | 05146299 | 6/1993 |
| JP | 07016094 | 1/1995 |
| WO | WO99/37820 | 7/1999 |

(Continued)

OTHER PUBLICATIONS

Walker et al., Proc. Natl. Acad. Sci. USA 89:392-396 (1992).

(Continued)

*Primary Examiner*—Teresa Strzelecka
(74) *Attorney, Agent, or Firm*—Harriet M. Strimpel

(57) ABSTRACT

Methods and a kit are provided for selectively and exponentially amplifying nucleic acids and include the use of a helicase preparation and a DNA polymerase such that the amplification can be performed isothermally.

47 Claims, 18 Drawing Sheets

FOREIGN PATENT DOCUMENTS

| WO | WO 00/41524 | 7/2000 |
| WO | WO 01/09347 A2 * | 2/2001 |
| WO | WO 01/025473 | 4/2001 |
| WO | WO 0202740 | 1/2002 |

OTHER PUBLICATIONS

Guatelli et al., Proc. Natl. Acad. Sci. USA 87:1874-1878 (1990).
Fire and Xu, Proc. Natl. Acad. Sci. USA 92:4641-4645 (1995).
Lui et al., J. Am. Chem. Soc. 118:1587-1594 (1996).
Lizardi et al., Nature Genetics 19:225-232 (1998).
Dean et al., Proc. Natl. Acad Sci. USA 99:5261-5266 (2002).
Barany, Proc. Natl. Acad Sci. USA 88:189-193 (1991).
Horn et al., Nucleic Acids Res. 25:4842-4849 (1997).
Cline et al., Nucleic Acids Res. 24:3546-3551 (1996).
Yamaguchi et al., J. Biol. Chem. 273:9197-9201 (1998).
Mechanic et al., J. Biol. Chem. 275:38337-38346 (2000).
Harmon and Kowalczykowski, J. Biol. Chem. 276:232-243 (2001).
Collins and McCarthy, Extremophiles 7:35-41 (2003).
Kaplan and Steitz, J. Biol. Chem. 274:6889-6897 (1999).
Grainge et al., Nucleic Acids Res. 31:4888-4898 (2003).
Caruthers and McKay, Curr. Opin. Struct. Biol. 12:123-133 (2002).
Soultanas and Wigley, Trends Biochem. Sci. 26:47-54 (2001).
Matson, J. Biol. Chem. 261:10169-10175 (1986).
Runyon and Lohman, J. Biol. Chem. 264:17502-17512 (1989).
Runyon et al., Proc. Natl. Acad. Sci. USA 87:6383-6387 (1990).
Lechner and Richardson, J. Biol. Chem. 258:11185-11196 (1983).
Bernstein and Richardson, J. Biol. Chem. 263:14891-14899 (1988).
Kim et al., J. Biol. Chem. 267:15032-15040 (1992).
Kim et al., J. Biol. Chem. 267:15022-15031 (1992).
Roman and Kowalczykowski, Biochemistry 28:2863-2873 (1989).
Wang et al., J. Biol. Chem. 275:507-513 (2000).
Taylor and Smith, Nature 423:889-893 (2003).
Dillingham et al., Nature 423:893-897 (2003).
Li et al., Nature 423:512-518 (2003).
Roychoudhury et al., Nucleic Acid Res. 6:1323-1333 (1979).
Kampke et al., Bioinformatics 17:214-225 (2001).
Lee et al., J. Mol. Biol. 316:19-34 (2002).
Jessing et al., J. Clin. Microbiol. 41:4095-4100 (2003).
Keohavong and Thilly, Proc. Natl. Acad. Sci. USA 86:9253-9257 (1989).
Miyoshi et al., Biochemistry 41:15017-15024 (2002).
Dong et al., Proc. Natl. Acad. Sci. USA 93:14456-14461 (1996).
Bradford, Anal. Biochem. 72:248-254 (1976).
Bao et al., Genome Res. 12:689-700 (2000).
Kuhn et al., DNA: Replication and Recombination, Cold Spring Harbor Symposia on Quantitative Biology vol. XLIII, Cold Spring Harbor Laboratory (1979).
Sambrook et al., Molecular Cloning: A Laboratory Manual, $2^{nd}$ ed., Cold Spring Harbor Press, Cold Spring Harbor, NY, 8.4-8.13 (2003).
Gorbalenya et al., Curr. Opin. Struct. Biol. 3:419-429 (1993).
Kornberg et al., DNA Replication, W.H. Freeman Company, NYC (2nd ed) (1992) pp. 355-378.
Ali et al., J. Mol. Biol. 293(4):815-830 (1999).

* cited by examiner

Genome Copies  $10^7$  $10^6$  $10^5$  $10^4$  $10^3$  $10^2$  10  0

FIGURE 15-1

```
TCGCGCGTTTCGGTGATGACGGTGAAAACCTCTGACACA
TGCAGCTCCCGGAGACGGTCACAGCTTGTCTGTAAGCG
GATGCCGGGAGCAGACAAGCCCGTCAGGGCGCGTCAGC
GGGTGTTGGCGGGTGTCGGGGCTGGCTTAACTATGCGG
CATCAGAGCAGATTGTACTGAGAGTGCACCATATGCGGT
GTGAAATACCGCACAGATGCGTAAGGAGAAATACCGC
ATCAGGCGCCATTCGCCATTCAGGCTGCGCAACTGTTGG
GAAGGGCGATCGGTGCGGGCCTCTTCGCTATTACGCCA
GCTGGCGAAGGGGGATGTGCTGCAAGGCGATTAAGTT
GGGTAACGCCAGGGTTTTCCCAGTCACGACGTTGTAAAA
CGACGGCCAGTGAATTGCATGCTCAGCTTGGCGTAATCA
TGGTCATAGCTGTTTCCTGTGTGAAATTGTTATCCGCTCA
CAATTCCACACAACATACGAGCCGGAAGCATAAAGTGTA
AAGCCTGGGGTGCCTAATGAGTGAGCTAACTCACATTAA
TTGCGTTGCGCTCACTGCCCGCTTTCCAGTCGGGAAACC
TGTCGTGCCAGCTGCATTAATGAATCGGCCAACGCGCG
GGGAGAGGCGGTTTGCGTATTGGGCGCTCTTCCGCTTC
CTCGCTCACTGACTCGCTGCGCTCGGTCGTTCGGCTGCG
GCGAGCGGTATCAGCTCACTCAAAGGCGGTAATACGGT
TATCCACAGAATCAGGGGATAACGCAGGAAAGAACATG
TGAGCAAAAGGCCAGCAAAAGGCCAGGAACCGTAAAAA
GGCCGCGTTGCTGGCGTTTTTCCATAGGCTCCGCCCCCC
TGACGAGCATCACAAAAATCGACGCTCAAGTCAGAGGT
GGCGAAACCCGACAGGACTATAAAGATACCAGGCGTTT
CCCCCTGGAAGCTCCCTCGTGCGCTCTCCTGTTCCGACC
CTGCCGCTTACCGGATACCTGTCCGCCTTTCTCCCTTCG
GGAAGCGTGGCGCTTTCTCATAGCTCACGCTGTAGGTAT
CTCAGTTCGGTGTAGGTCGTTCGCTCCAAGCTGGGCTGT
GTGCACGAACCCCCGTTCAGCCCGACCGCTGCGCCTTA
TCCGGTAACTATCGTCTTGAGTCCAACCCGGTAAGACAC
GACTTATCGCCACTGGCAGCAGCCACTGGTAACAGGATT
AGCAGAGCGAGGTATGTAGGCGGTGCTACAGAGTTCTT
GAAGTGGTGGCCTAACTACGGCTACACTAGAAGGACAG
TATTTGGTATCTGCGCTCTGCTGAAGCCAGTTACCTTCG
GAAAAAGAGTTGGTAGCTCTTGATCCGGCAAACAAACCA
```

FIGURE 15-2

```
CCGCTGGTAGCGGTGGTTTTTTTGTTTGCAAGCAGCAGA
TTACGCGCAGAAAAAAGGATCTCAAGAAGATCCTTTGA
TCTTTTCTACGGGGTCTGACGCTCAGTGGAACGAAAACT
CACGTTAAGGGATTTTGGTCATGAGATTATCAAAAAGGA
TCTTCACCTAGATCCTTTTAAATTAAAAATGAAGTTTTAA
ATCAATCTAAAGTATATGAGTAAACTTGGTCTGACAG
TTACCAATGCTTAATCAGTGAGGCACCTATCTCAGCGAT
CTGTCTATTTCGTTCATCCATAGTTGCCTGACTCCCCGTC
GTGTAGATAACTACGATACGGGAGGGCTTACCATCTGGC
CCCAGTGCTGCAATGATACCGCGAGACCCACGCTCACC
GGCTCCAGATTTATCAGCAATAAACCAGCCAGCCGGAAG
GGCCGAGCGCAGAAGTGGTCCTGCAACTTTATCCGCCTC
CATCCAGTCTATTAATTGTTGCCGGGAAGCTAGAGTAAG
TAGTTCGCCAGTTAATAGTTTGCGCAACGTTGTTGCCAT
TGCTACAGGCATCGTGGTGTCACGCTCGTCGTTTGGTAT
GGCTTCATTCAGCTCCGGTTCCCAACGATCAAGGCGAGT
TACATGATCCCCCATGTTGTGCAAAAAAGCGGTTAGCTC
CTTCGGTCCTCCGATCGTTGTCAGAAGTAAGTTGGCCGC
AGTGTTATCACTCATGGTTATGGCAGCACTGCATAATTC
TCTTACTGTCATGCCATCCGTAAGATGCTTTTCTGTGACT
GGTGAGTACTCAACCAAGTCATTCTGAGAATAGTGTATG
CGGCGACCGAGTTGCTCTTGCCCGGCGTCAATACGGGA
TAATACCGCGCCACATAGCAGAACTTTAAAAGTGCTCAT
CATTGGAAAACGTTCTTCGGGGCGAAAACTCTCAAGGAT
CTTACCGCTGTTGAGATCCAGTTCGATGTAACCCACTCG
TGCACCCAACTGATCTTCAGCATCTTTTACTTTCACCAGC
GTTTCTGGGTGAGCAAAAACAGGAAGGCAAAATGCCGC
AAAAAAGGGAATAAGGGCGACACGGAAATGTTGAATAC
TCATACTCTTCCTTTTTCAATATTATTGAAGCATTTATCA
GGGTTATTGTCTCATGAGCGGATACATATTTGAATGTAT
TTAGAAAAATAAACAAATAGGGGTTCCGCGCACATTTCC
CCGAAAAGTGCCACCTGACGTCTAAGAAACCATTATTAT
```

FIGURE 15-3

CATGACATTAACCTATAAAAATAGGCGTATCACGAGGCC
CTTTCGTC

FIGURE 16

ATGAGTAGGCGTGAAGTAAAAAATCAAACAAATATTTCT
AGAATTGAAGGAATTAAACCAAATGATGCTTATGTTGCT
TATGTATGTGTACAATGTAACAATTTGAATATGATAAATA
TTGGACAAAATTATTAGATCCAAGAGAGGCTTATGAAA
CACAAGAATGGAAATGTGAAAGATGTGGATTTTTACATA
GTAAAAATAATTCATTGTCTTATTCAAACTGGCCAGAAG
AAAGTAAAAAGAAAGGTTCTATTCCTGTACAAAGATTTT
GGCAAGCTTTTTTAGAGTATACAGAGAATAAAGAAG
CATATTGGAAACAATGTAATTGTTGTGGAAAATATTAC
CATTTTCCGCATTTAGCAAGCATATTGGTTTTGGCCCTCT
TGAAAGACAAATGGAATGTAGAGCTTGTAAGGGAGTGA
TAAATGCATTTTTAAATCCAGAAAGAACAGAAGATCAAT
TAAGAGAGTCAAATGTTAGGAGACGTGTTGCCGATTTGT
TTGTTAAAAAGAAAATAAATCTAAAGATGATGGATTTAT
TAAAGATTTATTTAAACGTTTTGGTTCAAAGTGCTTTAAA
ACAAAGAAATATCTAAATATTCATGATAGAAATTCTTGG
GCTATAGATCATATTTTACCATCAAAATATCTTTATCCTC
TTACAAAAGAAAATGCTGCACTATTATCTGTAGAAGCTA
ATTCCAATAAAAGAGATCGTTGGCCTTCAGAATTTTATAC
AAATAATGAATTAATAGAACTTGCTACAATAACAGGAGC
TGATTTACAATTATTCAAATAAACACCTATTATAAAT
CCAAATCTTACTGATGAGGATATAAATGCAGGTATTGAG
AATTATTTGTCTGTTCGTGAAAATTCAAACCTTGAGAAGC
GAGTAGCTGAAATAAAAAAATCATAATAGACTATCAAT
TAACGGATAAATTATCGAAAGCAACAAGAATTTACTTG
GTTTATCTTAA

HELICASE DEPENDENT AMPLIFICATION OF NUCLEIC ACIDS

CROSS REFERENCE

This application gains priority from U.S. provisional application Ser. No.: 60/412,298 filed Sep. 20, 2002 and U.S. provisional application Ser. No.: 60/446,662 filed Feb. 11, 2003 both applications hereby incorporated by reference.

BACKGROUND

Amplification of nucleic acids is widely used in research, forensics, medicine and agriculture. One of the best-known amplification methods is the polymerase chain reaction (PCR), which is a target amplification method (See for example, U.S. Pat. Nos. 4,683,195, 4,683,202 and 4,800, 159). A PCR reaction typically utilizes two oligonucleotide primers which are hybridized to the 5' and 3' borders of the target sequence and a DNA polymerase which can extend the annealed primers by adding on deoxynucleoside-triphosphates (dNTPs) to generate double-stranded products. By raising and lowering the temperature of the reaction mixture, the two strands of the DNA product are separated and can serve as templates for the next round of annealing and extension, and the process is repeated.

Although PCR has been widely used by researchers, it requires thermo-cycling to separate the two DNA strands. Several isothermal target amplification methods have been developed in the past 10 years. One of them is known as Strand Displacement Amplification (SDA). SDA combines the ability of a restriction endonuclease to nick the unmodified strand of its target DNA and the action of an exonuclease-deficient DNA polymerase to extend the 3' end at the nick and displace the downstream DNA strand. The displaced strand serves as a template for an antisense reaction and vice versa, resulting in exponential amplification of the target DNA (See, for example, U.S. Pat. Nos. 5,455,166 and 5,470,723). In the originally-designed SDA, the DNA was first cleaved by a restriction enzyme in order to generate an amplifiable target fragment with defined 5' and 3'-ends but the requirement of a restriction enzyme cleavage site limited the choice of target DNA sequences (See for example, Walker et. al., *Proc. Natl. Acad. Sci. USA* 89:392–396 (1992)). This inconvenience has been circumvented by the utilization of bumper primers which flank the region to be amplified (Walker et al. supra (1992)). SDA technology has been used mainly for clinical diagnosis of infectious diseases such as chlamydia and gonorrhea. One of the most attractive feature of SDA is its operation at a single temperature which circumvents the need for expensive instrumented thermal cycling. However, SDA is inefficient at amplifying long target sequences.

A second isothermal amplification system, Transcription-Mediated Amplification (TMA), utilizes the function of an RNA polymerase to make RNA from a promoter engineered in the primer region, and a reverse transcriptase, to produce DNA from the RNA templates. This RNA amplification technology has been further improved by introducing a third enzymatic activity, RNase H, to remove the RNA from cDNA without the heat-denaturing step. Thus the thermocycling step has been eliminated, generating an isothermal amplification method named Self-Sustained Sequence Replication (3SR) (See, for example, Guatelli eta., *Proc. Natl. Acad. Sci. USA* 87:1874–1878 (1990)). However, the starting material for TMA and 3SR is limited to RNA molecules.

A third isothermal target amplification method, Rolling Circle Amplification (RCA), generates multiple copies of a sequence for the use in in vitro DNA amplification adapted from in vivo rolling circle DNA replication (See, for example, Fire and Xu, *Proc. Natl. Acad Sci. USA* 92:4641–4645 (1995); Lui, et al., *J. Am. Chem. Soc.* 118: 1587–1594 (1996); Lizardi, et al., *Nature Genetics* 19:225–232 (1998), U.S. Pat. Nos. 5,714,320 and 6,235, 502). In this reaction, a DNA polymerase extends a primer on a circular template generating tandemly linked copies of the complementary sequence of the template (See, for example, Kornberg and Baker, DNA Replication, W. H. Freeman and Company, New York ($2^{nd}$ ed. (1992)). Recently, RCA has been further developed in a technique, named Multiple Displacement Amplification (MDA), which generates a highly uniform representation in whole genome amplification (See, for example, Dean et. al., *Proc. Natl. Acad Sci. USA* 99:5261–5266 (2002)).

Additional nucleic acid amplification methods include Ligase Chain Reaction (LCR), which is a probe amplification technology (See, for example, Barany, *Proc. Natl. Acad Sci. USA* 88:189–193 (1991)); and U.S. Pat. No. 5,494,810), and branched DNA (bDNA) technology (Horn et al., *Nucleic Acids Res.* 25:4842–4849 (1997)), which is a signal amplification technology.

The amplification methods mentioned above all have their limitations. For example, PCR and LCR require a thermocycler with associated instrumentation. Except for PCR, none of the other target amplification methods are capable of amplifying DNA targets having sufficient length to be useful for cloning genes and analysis of virulence factors and antibiotic resistant genes. Although PCR is able to amplify a target up to 10–20 kb, high mutation rates may limit the use of PCR-amplified products (Cline et al., *Nucleic Acids Res.* 24, 3546–3551 (1996)). Thus, to minimize the problem, a high-fidelity amplification method for long targets is needed. In addition, all present amplification methods require prior heat denaturation and annealing steps to produce primed templates for DNA polymerases. This adds extra time to the amplification process.

The potential uses for nucleic acid amplification techniques continues to grow. For example, nucleic acid arrays frequently utilize large numbers of amplification reactions. Detection of environmental contamination places demands on sensitivity and analytic power of diagnostic tests that include nucleic acid amplification procedures. Consequently, improvements in amplification methodology are desirable.

SUMMARY OF THE INVENTION

In an embodiment of the invention, a method is provided for exponentially and selectively amplifying a target nucleic acid that includes the steps of: providing single strand templates of the target nucleic acid to be amplified; adding oligonucleotide primers for hybridizing to the templates; synthesizing an extension product of the oligonucleotide primers which are complementary to the templates, by means of a DNA polymerase to form a duplex; contacting the duplex with a helicase preparation for unwinding the duplex; and repeating the above steps to exponentially and selectively amplify the target nucleic acid.

In additional embodiments of the invention, amplification may be isothermal and may be accomplished in the range of about 20° C.–75° C., preferably at room temperature.

In additional embodiments of the invention, the target nucleic acid may be either a single stranded nucleic acid, more particularly, a single stranded DNA or a single stranded RNA, or a double stranded nucleic acid, more particularly a double stranded DNA. When the nucleic acid is double stranded, it may be denatured by heat or enzymatically to form a single strand template for DNA polymerase dependent amplification. In addition, the target nucleic acid may have a size in the range of about 50 bp to 100 kb.

In additional embodiments of the invention, the oligonucleotide primers used in the method of amplification are a pair of oligonucleotide primers wherein one primer hybridizes to 5'-end and one primer hybridizes to 3'-end of the target nucleic acid to be selectively amplified. Under circumstances of multiplexing, multiple primer pairs may be used to amplify multiple target nucleic acids in the same reaction mixture. In addition, the oligonucleotide primers may have a length and a GC content so that the melting temperature of the oligonucleotide primers is 10° C.–30° C. above the reaction temperature of hybridization during amplification.

In additional embodiments of the invention, a DNA polymerase is selected from a Klenow fragment of *E. coli* DNA polymerase I, T7 DNA polymerase (Sequenase) and Bst polymerase large fragment. Preferably, the DNA polymerase lacks 5' to 3' exonuclease activity and possesses strand displacement activity.

In additional embodiments of the invention, the helicase preparation may include a single helicase or a plurality of helicases. The helicase or helicases in the preparation may be selected from the class of 3' to 5' helicases or the class of 5' to 3' helicases. More particularly, the helicase preparation may include a helicase from superfamily 1–4 or an AAA$^+$ helicase. The helicase may be a hexameric helicase or a monomeric or dimeric helicase. More particularly, the helicase may be a UvrD helicase or homolog thereof, for example a thermostable helicase or homolog thereof.

In additional embodiments of the invention, the helicase preparation may include one or more helicases selected from the group consisting of: *E. coli* UvrD helicase, Tte-UvrD helicase, T7 Gp4 helicase, RecBCD helicase, DnaB helicase, MCM helicase, Rep helicase, RecQ helicase, PcrA helicase, SV40 large T antigen helicase, Herpes virus helicase, yeast Sgs1 helicase, DEAH_ATP-dependent helicases and Papillomavirus helicase E1 protein and homologs thereof.

Additionally, the helicase preparation includes a nucleotide triphosphate (NTP) or deoxynucleotide triphosphate (dNTP) for example, adenosine triphosphate (ATP), deoxythymidine triphosphate (dTTP) or deoxyadenosine triphosphate (dATP). A suitable concentration for the energy source is in the range of about 0.1–50 mM.

In additional embodiments of the invention, the helicase preparation includes a single strand binding protein, for example, T4 gene 32 SSB, *E.coli* SSB, T7 gene 2.5 SSB, phage phi29 SSB and derivatives therefrom and an accessory protein for example, MutL.

Embodiments of the invention include detecting pathogens in biological samples by helicase dependent amplification, where the target nucleic acid is a nucleic acid from the pathogen. Alternatively, sequence variations in chromosomal DNA can be determined when the target nucleic acid is a fragment of chromosomal DNA. This approach can be used to detect single nucleotide polymorphisms in the target nucleic acid from different sources.

In an embodiment of the invention, a kit is provided that includes a helicase preparation and a nucleotide triphosphate or deoxynucleotide triphosphate and a DNA polymerase and instructions for performing helicase dependent amplification. The kit may be used for example in the field, in the laboratory with standard equipment, or for high throughput screening of samples.

In an embodiment of the invention, a method is provided for determining whether a helicase for use in a helicase preparation is suited for exponentially and selectively amplifying a target nucleic acid, which includes the steps of: preparing a helicase preparation comprising the helicase, an NTP or dNTP, a buffer, wherein the buffer of Tris-acetate or Tris-HCl providing a pH in the range of about pH 6.0–9.0, and a concentration of NaCl or KCl in a concentration range of 0–200 mM and optionally a single stranded binding protein and/or an accessory protein; adding a target nucleic acid in varying concentrations or copy number, oligonucleotide primers, four dNTPs and a DNA polymerase to the helicase preparation; incubating the mixture at a temperature between about 20° C. and 75° C.; and analyzing the amplified DNA to determine whether selective and exponential amplification has occurred.

Composition of the reaction mixture, conditions of the reaction and concentration of the reactants can be varied within certain ranges provided herein to identify the optimum conditions for helicase dependent amplification.

HDA reactions were performed using an UvrD helicase preparation containing *E. coli* UvrD helicase, *E. coli* MutL, T4 Gp32 and ATP plus a polymerases, two primers (1224 and 1233), and target DNA of different lengths in plasmid pAH1. The amplification product was analyzed by gel electrophoresis on a 3% LMP agarose gel. Lane 1: 110-bp, Lane 2: 200 bp; lane 3: 300 bp; lane 4: 400 bp; lane 5: 650 bp length target DNA. M: 100 bp DNA ladder sizing marker.

Figure 5:
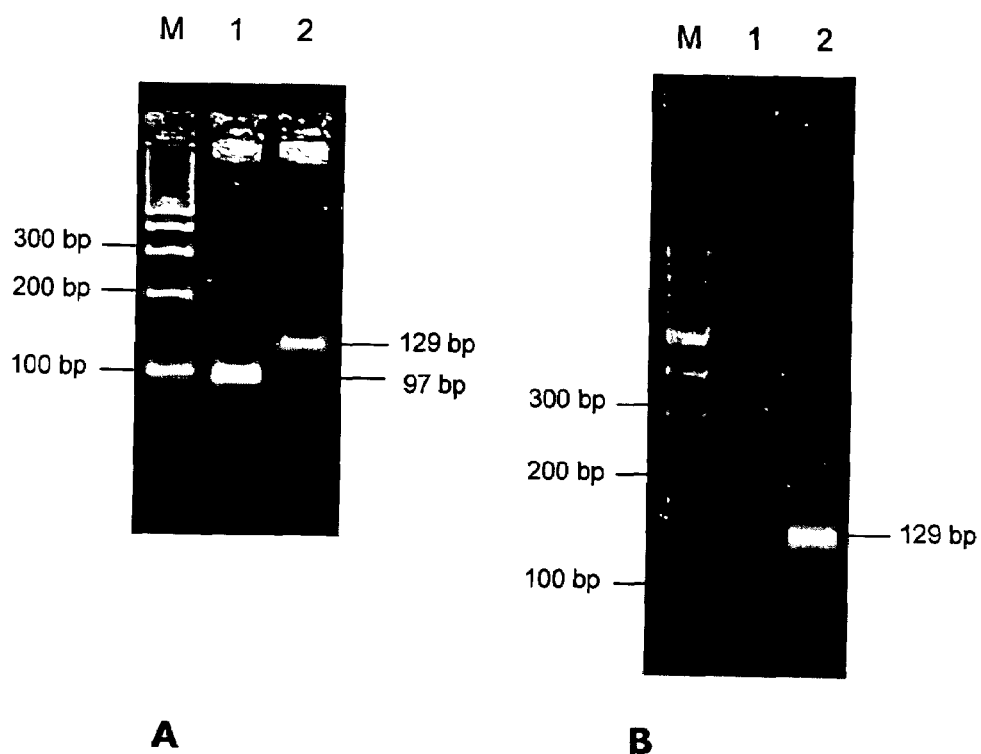

FIG. 5. Amplification of target sequences from bacterial genomic DNA using two different polymerases. Target nucleic acids were amplified from *T. denticola* genomic DNA using a UvrD helicase preparation containing *E. coli* UvrD helicase, *E. coli* MutL, T4 Gp32 and ATP plus two different polymerases. Amplification products were analyzed by gel electrophoresis on a 3% LMP agarose gel.

FIG. 5A: HDA using exo$^-$ Klenow Fragment of DNA polymerase I;

Lane 1: Product of HDA using primer-58861 and primer-58862. Lane 2: Product of HDA with primer-58861 and primer-58863.

FIG. 5B: HDA using T7 sequenase and primers-58861 and 58863: Lane 1: 1.5 units of T7 Sequenase; Lane 2: 3.5 units of T7 Sequenase; and Lane M shows a 100 bp DNA ladder used as sizing marker.

Figure 6:
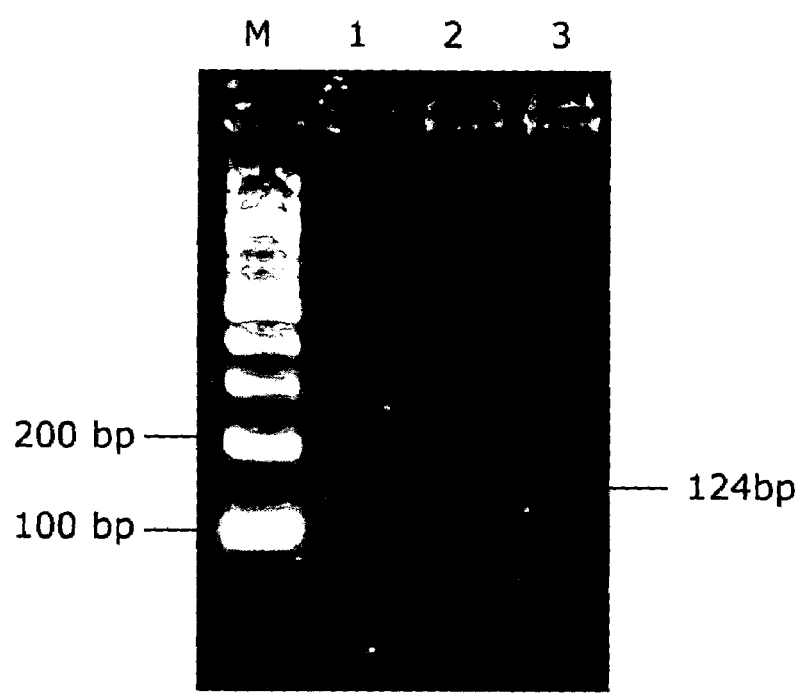

FIG. 6. Amplification of target sequences from human genomic DNA.

HDA reaction was carried out using a helicase preparation containing E. coli UvrD helicase, MutL, T4 Gp32, and ATP plus a DNA polymerases, two primers and human genomic DNA. HDA products were analyzed by gel electrophoresis using a 3% LMP agarose gel. M: 100 bp DNA ladder used as sizing marker. HDA product from: 100 ng initial human genomic DNA (Lane 1) from 150 ng initial human genomic DNA (Lane 2), from 200 ng initial human genomic DNA (lane 3).

Figure 7:

FIG. 7. Amplification of target sequences coupled to cDNA synthesis (RT amplification).

The HDA reaction was coupled with cDNA synthesis. The first strand cDNA (RNA/DNA hybrid) was further amplified by HDA using a helicase preparation containing E. coli UvrD helicase, MutL, T4 Gp32, and ATP plus a DNA polymerases, and two primers which are specific to the rat GAPDH gene. The amplification products: 2 µl first cDNA strand (Lane 1), 4 µl first cDNA strand (Lane 2) were analyzed by gel electrophoresis on a 3% LMP agarose gel. M: ØX174 DNA-HaeIII DNA ladder.

Figure 8:
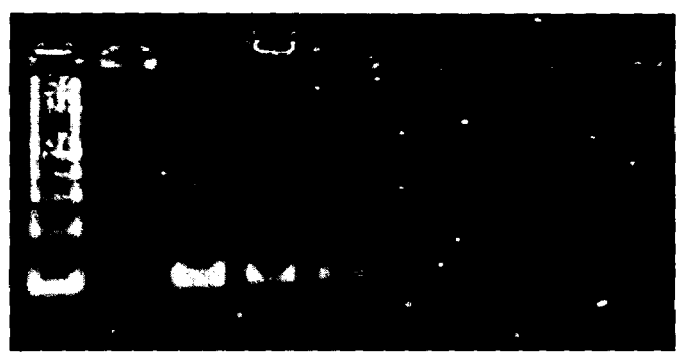

FIG. 8. Sensitivity of amplification of various copy numbers of target sequences from bacterial genomic DNA. HDA reactions were carried out using a helicase preparation containing E. coli UvrD helicase, MutL, T4 Gp32, and ATP plus a DNA polymerases, two primers (primer-58861 and primer-58862), and various amount of Treponema denticola genomic DNA. The amplification products were analyzed by gel electrophoresis on a 3% LMP agarose gel. The number of copies of the single Treponema denticola chromosome initially present in each HDA reaction is shown above each lane in descending numbers of $10^7$, $10^6$, $10^5$, $10^4$, $10^3$, $10^2$, 10 and 0.

Figure 9:
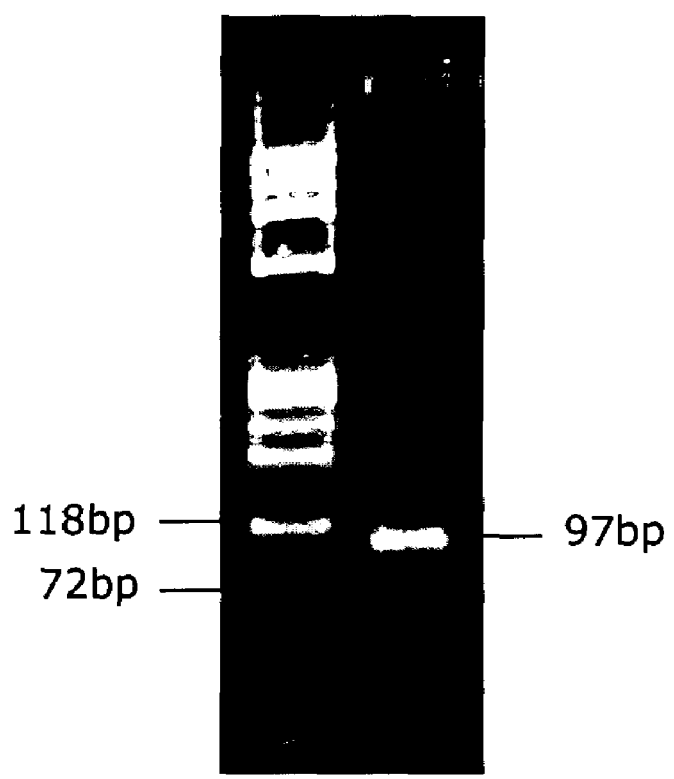

FIG. 9. Amplification of target sequences from bacterial genomic DNA without prior denaturation.

HDA reaction was carried out using a helicase preparation containing E. coli UvrD helicase, MutL, T4 Gp32, and ATP plus a DNA polymerases, two primers (primer-58861 and primer-58862), and Treponema denticola genomic DNA. HDA products were analyzed by gel electrophoresis using a 3% LMP agarose gel. M: ØX174 DNA-HaeIII DNA ladder used as sizing marker.

Figure 10:
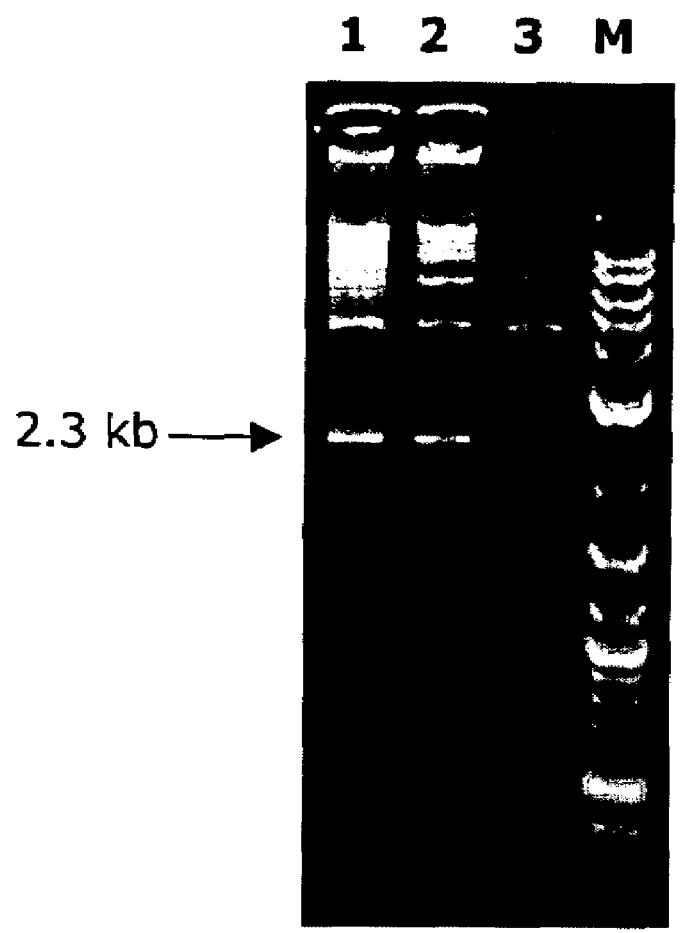

FIG. 10. Amplification of a 2.3-Kb target DNA using a single helicase (T7 Gp4B helicase) or two helicases (UvrD helicase and T7 Gp4B helicase).

HDA reactions were performed using two primers (1224 and 1233) and plasmid pCR-Rep in the presence of the T7 Gp4B helicase preparation including T7 Gp4B helicase and T7 Gp2.5 SSB (Lane 1): in the presence of a helicase preparation containing both T7 Gp4B helicase and UvrD helicase (Lane 2): negative control, no helicase (Lane 3). M: 2-log DNA ladder used as sizing marker. The products of HDA are shown by 1% gel electrophoresis.

Figure 11:
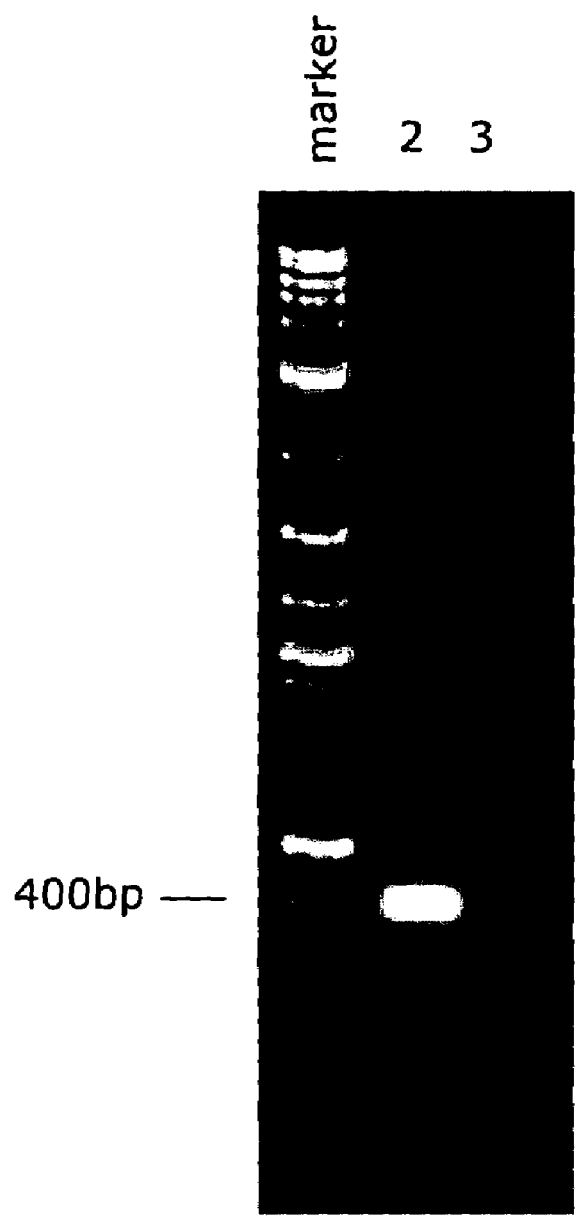

FIG. 11. Amplification of 400 bp target DNA using RecBCD helicase.

HDA reactions were performed using a RecBCD helicase preparation containing $RecB^{D1067A}CD$ helicase, T4 Gp32 and ATP plus a polymerases (T7 Sequenase), two primers (1224 and 1233), and target DNA. Gel electrophoresis of HDA products on a 1% agarose gel is shown where Lane 2 shows the amplification product from a helicase preparation containing both $RecB^{D1067A}CD$ helicase and T7 Sequenase and Lane 3 shows a negative control with no helicase. Marker: 2-log DNA ladder used as sizing marker (NEB).

Figure 12:
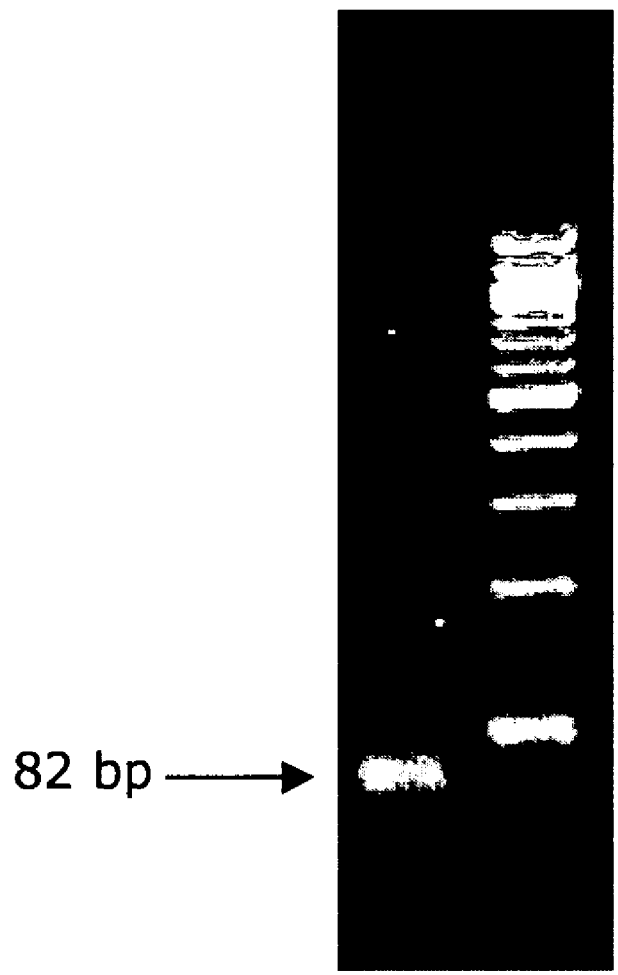

FIG. 12. Amplification of a target sequence from bacterial genomic DNA by thermostable HDA.

HDA reaction was carried out using a helicase preparation containing the thermostable Tte-UvrD helicase, T4 Gp32, and dATP plus a thermostable Bst DNA polymerases, two primers and T. denticola genomic DNA. The amplification product was analyzed by gel electrophoresis on a 2% LMP agarose gel. M: 100 bp DNA ladder used as sizing marker (NEB). Lane 1: 82 bp product.

Figure 13:
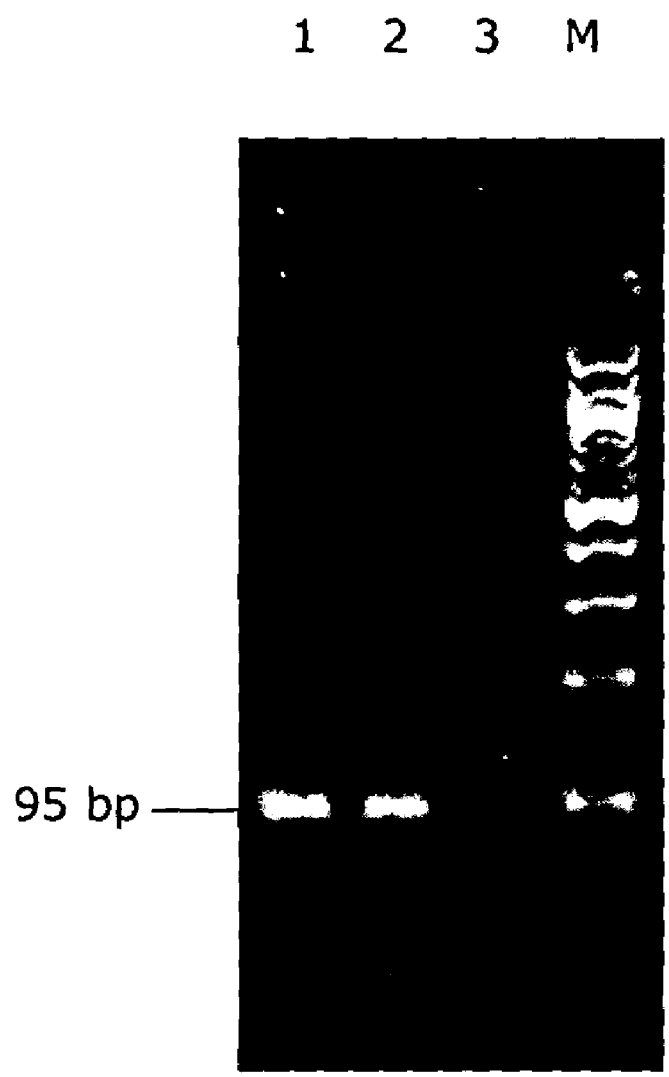

FIG. 13. Amplification of a target sequence from the genomic DNA of Neisseria gonorrhoeae by thermostable helicases absent some or all accessory proteins.

HDA reaction was carried out using various helicase preparations plus a thermostable Bst DNA polymerases, two primers and Neisseria gonorrhoeae genomic DNA. One helicase preparation contains the thermostable Tte-UvrD helicase, T4 Gp32, and dATP (Lane 1). The second helicase preparation contains the thermostable Tte-UvrD helicase and dATP (Lane 2). In a control reaction, only T4 Gp 32 and ATP is present in the preparation (Lane 3). M: 100 bp DNA ladder used as sizing marker (NEB).

Figure 14:
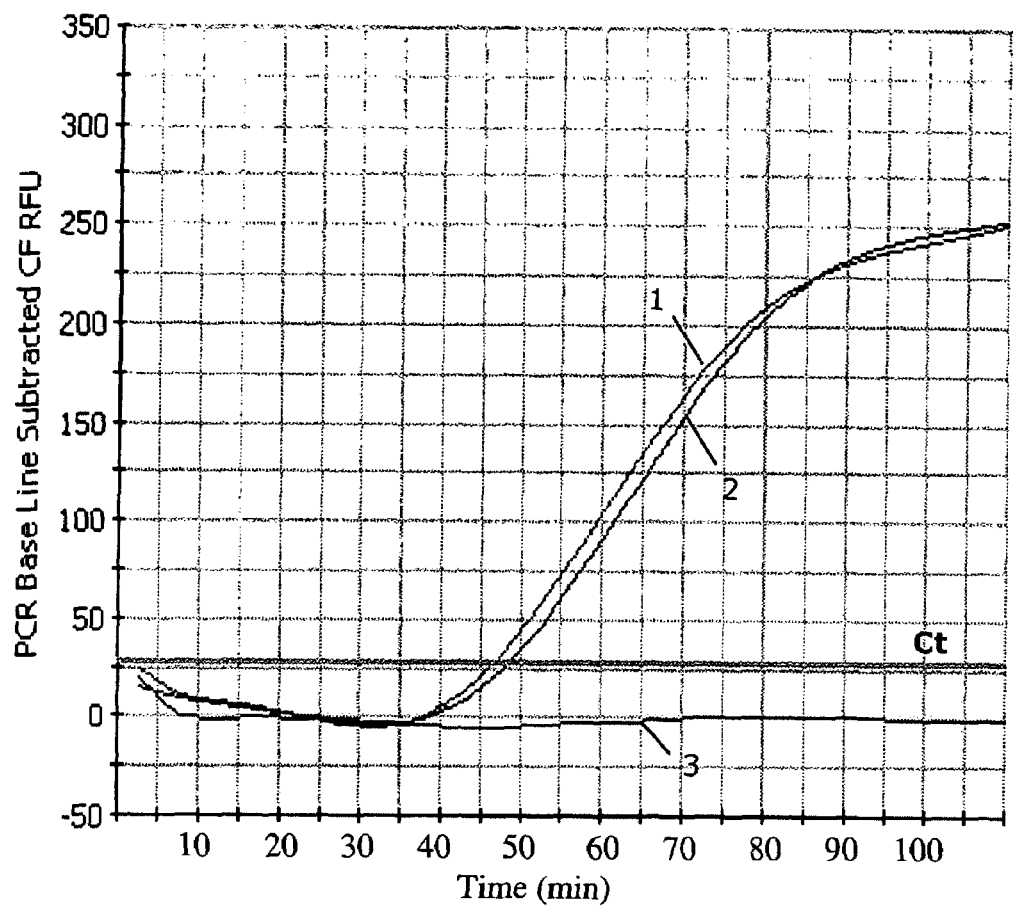

FIG. 14. Real-time detection of an oral pathogen, T. denticola, by HDA method.

HDA reaction was carried out using an UvrD helicase preparation containing E. coli UvrD helicase, MutL, T4 Gp32, and ATP plus a DNA polymerases, T. denticola genomic DNA, a fluorescent labeled LUX primer (Invitrogen) and a reverse primer. The amplification product was detected in real-time by measuring FAM fluorescent signals using a real-time PCR machine, iCycler, (Bio-Rad). 1 & 2: two identical reactions in which HDA was performed in the presence of genomic DNA, primers, and the UvrD HDA system. 3: HDA was performed similar to 1 & 2, except the genomic DNA was absent (negative control).

FIG. 15. Sequence of plasmid pAH1 (SEQ ID NO:9).

FIG. 16. Sequence of earRI gene T. denticola (SEQ ID NO:10).

DETAILED DESCRIPTION OF EMBODIMENTS

Figure 1:
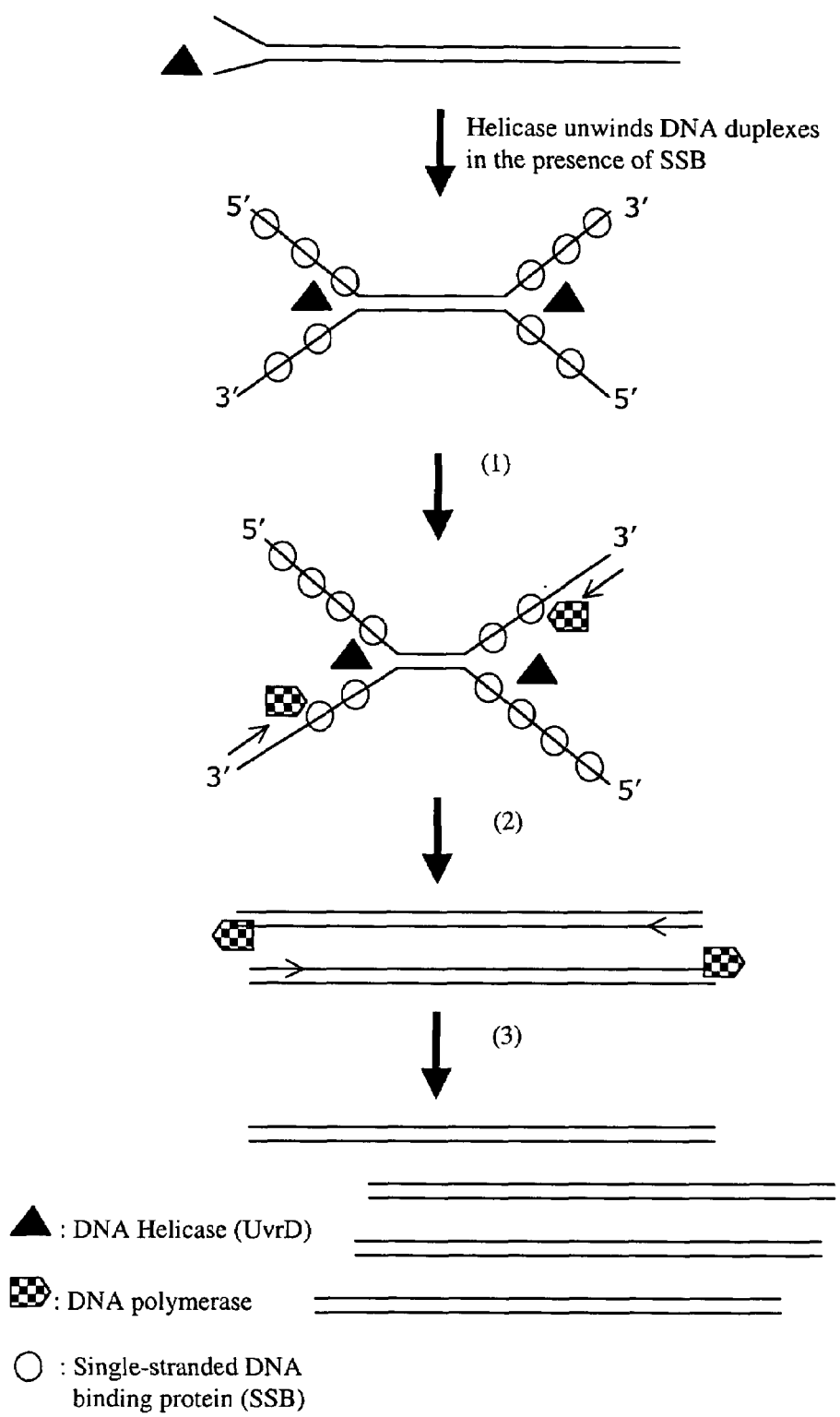
FIG. 1. Schematic Diagram of Helicase Displacement Amplification where (1) refers to primers annealing to single strand DNA, (2) refers to DNA polymerase extending the primers, where one duplex is amplified to two duplexes, and (3) refers to repeating the process to result in exponential amplification.

A novel amplification methodology is described herein which is referred to as "Helicase Dependent Amplification" (HDA). Helicase-Dependent Amplification (HDA) is based on the unwinding activity of a DNA helicase. This novel process uses a helicase rather than heat to separate the two strands of a DNA duplex generating single-stranded templates for the purpose of in vitro amplification of a target nucleic acid. Sequence-specific primers hybridize to the templates and are then extended by DNA polymerases to amplify the target sequence. This process repeats itself so that exponential amplification can be achieved at a single temperature (FIG. 1).

This amplification system has improved characteristics over amplification procedures described in the prior art. These improvements include for example, the ability to amplify long target sequences of nucleic acids isothermally with high fidelity.

HDA relies on one or more helicases to separate (melt, or unwind) two strands of a nucleic acid duplex. HDA further utilizes a DNA or RNA polymerase to extend primers which are hybridized to single stranded nucleotide sequences to form complementary primer extension products. This process repeats itself so that exponential amplification can be achieved at a single temperature. Some advantages of the present embodiments over amplification procedures in the prior art include the ability to isothermally amplify long target sequences of DNA and RNA (longer than about 200 nucleotides more particularly, greater than about 500 nucleotides, more particularly greater than about 1000 nucleotides, more particularly, greater than 2000 nucleotides, more particularly up to about 50,000 nucleotides, more particularly as much as about 100,000 nucleotides) and the ability to amplify target sequences at one temperature from the beginning to the end.

Definitions

For convenience, certain terms employed in the specification, examples and appended claims are collected here.

The term "Nucleic acid" refers to double stranded or single stranded DNA, RNA molecules or DNA/RNA hybrids. Those molecules which are double stranded nucleic acid molecules may be nicked or intact. The double stranded or single stranded nucleic acid molecules may be linear or circular. The duplexes may be blunt ended or have single stranded tails. The single stranded molecules may have secondary structure in the form of hairpins or loops and stems. The nucleic acid may be isolated from a variety of sources including the environment, food, agriculture, fermentations, biological fluids such as blood, milk, cerebrospinal fluid, sputum, saliva, stool, lung aspirates, swabs of mucosal tissues or tissue samples or cells. Nucleic acid samples may obtained from cells or viruses and may include any of: chromosomal DNA, extra chromosomal DNA including plasmid DNA, recombinant DNA, DNA fragments, messenger RNA, transfer RNA, ribosomal RNA, double stranded RNA or other RNAs that occur in cells or viruses. The nucleic acid may be isolated, cloned or synthesized in vitro by means of chemical synthesis. Any of the above described nucleic acids may be subject to modification where individual nucleotides within the nucleic acid are chemically altered (for example, by methylation). Modifications may arise naturally or by in vitro synthesis. The term "duplex" refers to a nucleic acid molecule that is double stranded in whole or part.

The term "target nucleic acid" refers to a whole or part of nucleic acid to be selectively amplified and which is defined by 3' and 5' boundaries. The target nucleic acid may also be referred to as a fragment or sequence that is intended to be amplified. The size of the target nucleic acid to be amplified may be, for example, in the range of about 50 bp to about 100 kb including a range of above 100–5000 bp. The target nucleic acid may be contained within a longer double stranded or single stranded nucleic acid. Alternatively, the target nucleic acid may be an entire double stranded or single stranded nucleic acid.

The terms "melting", "unwinding" or "denaturing" refer to separating all or part of two complementary strands of a nucleic acid duplex.

The term of "hybridization" refers to binding of an oligonucleotide primer to a region of the single-stranded nucleic acid template under the conditions in which primer binds only specifically to its complementary sequence on one of the template strands, not other regions in the template. The specificity of hybridization may be influenced by the length of the oligonucleotide primer, the temperature in which the hybridization reaction is performed, the ionic strength, and the pH.

The term "primer" refers to a single stranded nucleic acid capable of binding to a single stranded region on a target nucleic acid to facilitate polymerase dependent replication of the target nucleic acid.

The term "accessory protein" refers to any protein capable of stimulating helicase activity. For example, E. coli MutL protein is an accessory protein (Yamaguchi et al. *J. Biol. Chem.* 273:9197–9201 (1998); Mechanic et al., *J. Biol. Chem.* 275:38337–38346 (2000)) for enhancing UvrD helicase melting activity. In embodiments of the method, accessory proteins are desirable for use with selected helicases. In alternative embodiments, unwinding of nucleic acids may be achieved by helicases in the absence of accessory proteins.

The term "cofactor" refers to small-molecule agents that are required for the helicase unwinding activity. Helicase cofactors include nucleoside triphosphate (NTP) and deoxynucleoside triphosphate (dNTP) and magnesium (or other divalent cations). For example, ATP (adenosine triphosphate) may be used as a cofactor for UvrD helicase at a concentration in the range of 0.1–100 mM and preferably in the range of 1 to 10 mM (for example 3 mM). Similarly, dTTP (deoxythymidine triphosphate) may be used as a cofactor for T7 Gp4B helicase in the range of 1–10 mM (for example 3 mM).

The term "helicase" refers here to any enzyme capable of unwinding a double stranded nucleic acid enzymatically. For example, helicases are enzymes that are found in all organisms and in all processes that involve nucleic acid such as replication, recombination, repair, transcription, translation and RNA splicing. (Kornberg and Baker, DNA Replication, W. H. Freeman and Company ($2^{nd}$ ed. (1992)), especially chapter 11). Any helicase that translocates along DNA or RNA in a 5' to 3' direction or in the opposite 3' to 5' direction may be used in present embodiments of the invention. This includes helicases obtained from prokaryotes, viruses, archaea, and eukaryotes or recombinant forms of naturally occurring enzymes as well as analogues or derivatives having the specified activity. Examples of naturally occurring DNA helicases, described by Kornberg and Baker in chapter 11 of their book, DNA Replication, W. H. Freeman and Company ($2^{nd}$ ed. (1992)), include *E. coli* helicase I, II, III, & IV, Rep, DnaB, PriA, PcrA, T4 Gp41helicase, T4 Dda helicase, T7 Gp4 helicases, SV40 Large T antigen, yeast RAD. Additional helicases that may be useful in HDA include RecQ helicase (Harmon and Kowalczykowski, *J. Biol. Chem.* 276:232–243 (2001)), thermostable UvrD helicases from *T. tengcongensis* (disclosed in this invention, Example XII) and *T. thermophilus* (Collins and McCarthy, *Extremophiles.* 7:35–41. (2003)), thermostable DnaB helicase from *T. aquaticus* (Kaplan and Steitz, *J. Biol. Chem.* 274:6889–6897 (1999)), and MCM helicase from archaeal and eukaryotic organisms ((Grainge et al., *Nucleic Acids Res.* 31:4888–4898 (2003)).

Examples of helicases for use in present embodiments may also be found at the following web address: http://blocks.fhcrc.org (Get Blocks by Keyword: helicase). This site lists 49 Herpes helicases, 224 DnaB helicases, 250 UvrD-helicases and UvrD/Rep helicases, 276 DEAH_ATP-dependent helicases, 147 Papillom_E1 Papillomavirus helicase E1 protein, 608 Viral helicase1 Viral (superfamily 1) RNA helicases and 556 DEAD_ATP-dependent helicases. Examples of helicases that generally replicate in a 5' to 3' direction are T7 Gp4 helicase, DnaB helicase and Rho helicase, while examples of helicases that replicate in the 3'-5' direction include UvrD helicase, PcrA, Rep, NS3 RNA helicase of HCV.

In a preferred embodiment of the invention, the helicase is provided in a "helicase preparation". The helicase preparation refers to a mixture of reagents which when combined with a DNA polymerase, a nucleic acid template, four deoxynucleotide triphosphates, and primers are capable of achieving isothermal, exponential and specific nucleic acid amplification in vitro.

More particularly, the helicase preparation includes a helicase, an energy source such as a nucleotide triphosphate (NTP) or deoxynucleotide triphosphate (dNTP), and a single strand DNA binding protein (SSB). One or more additional reagents may be included in the helicase preparation, where these are selected from the following: one or more additional helicases, an accessory protein, small molecules, chemical reagents and a buffer.

Where a thermostable helicase is utilized in a helicase preparation, the presence of a single stranded binding protein is optional.

The term "HDA system" has been used herein to describe a group of interacting elements for performing the function of amplifying nucleic acids according to the Helicase-Dependent Amplification method described herein. The HDA system includes an helicase preparation, a polymerase and optionally a topoisomerase.

For example, the UvrD HDA system may be constituted by mixing together, a UvrD helicase preparation (for example, an $E.coli$ UvrD helicase preparation or a Tte-UvrD helicase preparation) and a DNA polymerase such as $Exo^{31}$ Klenow Fragment, DNA polymerase Large fragment, $Exo^+$ Klenow Fragment or T7 Sequenase.

Another example is the T7 HDA system which includes a T7 helicase preparation (T7 Gp4B helicase, T7 Gp2.5 SSB, and dTTP), and T7 Sequenase.

Another example is RecBCD HDA system which includes a RecBCD preparation (RecBCD helicase with T4gp 32) and T7 Sequenase.

Any selected HDA system may be optimized by substitution, addition, or subtraction of elements within the mixture as discussed in more detail below.

The term "HDA" refers to Helicase Dependent Amplification which is an in vitro method for amplifying nucleic acids by using a helicase preparation for unwinding a double stranded nucleic acid to generate templates for primer hybridization and subsequent primer-extension. This process utilizes two oligonucleotide primers, each hybridizing to the 3'-end of either the sense strand containing the target sequence or the anti-sense strand containing the reverse-complementary target sequence. The HDA reaction is a general method for helicase-dependent nucleic acid amplification.

"Isothermal amplification" refers to amplification which occurs at a single temperature. This does not include the single brief time period (less than 15 minutes) at the initiation of amplification which may be conducted at the same temperature as the amplification procedure or at a higher temperature.

How Helicases Work

Helicases use the energy of nucleoside triphosphate (for example ATP) hydrolysis to break the hydrogen bonds that hold the strands together in duplex DNA and RNA (Kornberg and Baker, DNA Replication, W. H. Freeman and Company ($2^{nd}$ ed. (1992)), especially chapter 11). Helicases are involved in every aspect of nucleic acid metabolism in the cell such as DNA replication, DNA repair and recombination, transcription, and RNA processing. This widespread usage may be reflected by the large numbers of helicases found in all living organisms.

Classification of Helicases

Helicases have been classified according to a number of different characteristics. For example, a feature of different helicases is their oligomeric structure including helicases with single or multimeric structures. For example, one family of helicases is characterized by hexameric structures while another family consists of monomeric or dimeric helicases.

Another characteristic of helicases is the occurrence of conserved motifs. All helicases have the classical Walker A and B motifs, associated with ATP-binding and $Mg^{2+}$-binding (reviewed in Caruthers and McKay. Curr. Opin. Struct. Biol. 12:123–133 (2002), Soultanas and Wigley. Trends Biochem. Sci. 26:47–54 (2001)). Helicases have been classified into several superfamilies (Gorbalenya and Koonin. Curr. Opin. Struct. Biol. 3:419–429 (1993)) according to the number of helicase signature motifs and differences in the consensus sequences for motifs. superfamilies 1 and 2 have seven characteristic helicase signature motifs and include helicases from archaea, eubacteria, eukaryotes and viruses, with helicases unwinding duplex DNA or RNA in either 3' to 5' direction or 5' to 3' direction. Examples of superfamily 1 helicases include the *E. coli* UvrD helicase, the *T. tengcongensis* UvrD helicase, and the B subunit of RecBCD. Superfamily 3 has three motifs and superfamily 4 has five motifs. Examples of superfamily 4 helicases include the T7 Gp4 helicase and DnaB helicases. A new family different from those canonical helicases is the $AAA^+$ family (the extended family of ATPase associated with various cellular activities).

A third type of classification relates to the unwinding directionality of helicases i.e. whether the helicase unwinds the nucleic acid duplex in a 5'-3' direction (such as T7 Gp4 helicase) or in a 3'-5' direction (such UvrD helicase) based on the strand on which the helicase binds and travels.

Figure 3:
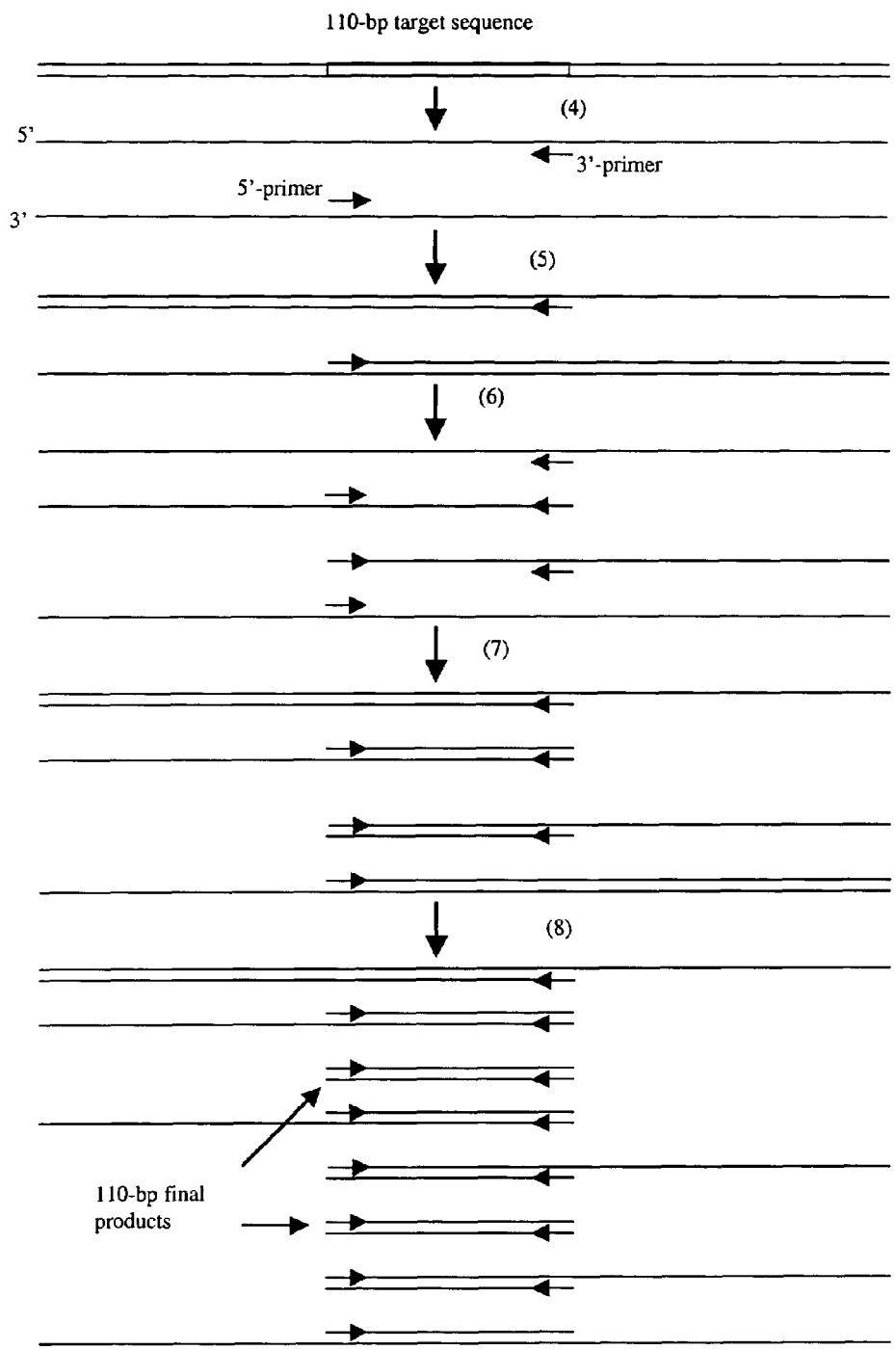
FIG. 3. Schematic diagram of selectively amplification of a target sequence from a large DNA molecule containing that sequence by HDA where (4) is dsDNA separation/Primer annealing, (5) is Primer extension by a polymerase, (6) is unwinding by a Helicase and subsequent Primer annealing, (7) is primer extension by a DNA polymerase and (8) is unwinding, annealing, and extension.

A fourth type of classification relates to whether a helicase preferably unwinds blunt ended nucleic acid duplexes or duplexes with forks or single stranded tails. Blunt-ended nucleic acid duplexes may not be required in the first cycle of helicase-dependent amplification but are desirable in subsequent cycles of amplification because along with the progress of the amplification reaction the blunt-ended target fragment becomes the dominant species (FIG. 3). These blunt-ended target nucleic acids form template substrates for subsequent rounds of amplification (FIG. 3).

To accomplish HDA described herein, a helicase classified according to any of the above is suitable for nucleic acid amplification. Indeed, Examples II–IX, X, XI and XII demonstrate a sample of the diversity of helicases that can be used according to the present methods to achieve helicase dependent amplification.

Example I describes a UvrD helicase preparation. UvrD helicase is a single-stranded DNA dependent ATPase activity that results in unwinding with a 3' to 5' polarity (Matson, J. Biol. Chem. 261:10169–10175 (1986)) and is involved in both DNA repair and recombination. In vivo, UvrD interacts with a second protein, MutL. MutL is the master coordinator of the mismatch repair pathway and dramatically stimulates the unwinding reaction catalyzed by UvrD (See, for example, Yamaguchi et al., J. Biol. Chem. 273, 9197–9201 (1998); Mechanic et al., J. Biol. Chem. 275, 38337–38346 (2000)). Examples XII and XIII show that an accessory protein is not always necessary in an optimized helicase preparation although it may preferably be used for some helicases such as UvrD. The requirement of an accessory protein for a particular helicase in HDA can be readily determined using an assay such as described in Examples II to V and analyzing the HDA product by gel electrophoresis.

*E. coli* UvrD helicase is a superfamily 1 helicase. *E. coli* UvrD helicase is able to unwind blunt-ended DNA duplexes as well as nicked circular DNA molecules (Runyon and Lohman, *J. Biol. Chem.* 264:17502–17512 (1989)). At low concentrations of UvrD, optimum unwinding requires a 3'-single stranded DNA tail but at higher concentrations, the unwinding can be initiated at nicks or blunt ends (Runyon, et al., *Proc. Natl. Acad. Sci. USA* 87:6383–6387 (1990)).

In another example of HDA, T7 gene 4 protein is used in a helicase preparation to amplify a target nucleic acid. T7 gene 4 protein is a hexameric replicative helicase which contains both a primase activity and a 3' to 5' helicase activity (Lechner and Richardson, *J. Biol. Chem.* 258: 11185–11196 (1983)). The amino-terminal truncated version of gene 4 protein, T7 gene 4B protein (T7 Gp4B helicase), only contains DNA helicase activity. The cloning and purification of the T7 Gp4B helicase has been described by Bernstein and Richardson (*J. Biol. Chem.* 263:14891–14899 (1988)). T7 gene 2.5 protein is a single strand DNA binding protein and it stimulates T7 DNA polymerase activity (Kim et al., *J. Biol. Chem.* 267:15032–15040 (1992)). The preparation of T7 Gp2.5 SSB has been described previously (Kim et al., *J. Biol. Chem.* 267:15022–5031 (1992)).

In another example of HDA, *E. coli* RecBCD protein is used in helicase preparation. *E. coli* RecBCD is a protein complex containing one superfamily 1 helicase (RecB) and one 5' to 3' helicase (RecD), is used to amplify a target fragment. *E.coli* RecBCD helicase is a trimeric, multifunctional enzyme, which is both an ATP-dependent helicase and a DNA nuclease (Roman and Kowalczykowski, *Biochemistry*. 28:2863–2873 (1989)). The RecB subunit possesses a 3' to 5' DNA helicase activity and also an exonuclease activity. The exonuclease activity can be abolished by site directed mutagenesis resulting in an exonuclease deficient RecB$^{D1067A}$CD which is able to unwind duplex DNA without degradation (Wang et al., *J. Biol. Chem.* 275, 507–513 (2000)). RecD protein is also a DNA helicase which possesses a 5' to 3' polarity (Taylor and Smith, *Nature* 423, 889–893 (2003)). RecB and RecD helicases are both active in intact RecBCD via a bipolar translocation model. The two DNA helicases are complementary, travel with opposite polarities, but in the same direction, on each strand of the antiparallel DNA duplex. This bipolar motor organization helps to explain its exceptionally high speed (500–1000 bp/sec) and processivity (>30 kb per binding event); Dillingham et al., *Nature* 423, 893–897 (2003)).

In another example of HDA, a hexameric replicative helicase, T7 Gp4 helicase, is used in a helicase preparation to amplify a target fragment longer than one kb. T7 Gp4 helicase belongs to superfamily 4 whose member including several hexameric helicase such as DnaB and T4 Gp41 and these helicases have rapid unwinding rates and a high degree of processivity. These helicases recognize single-stranded tails at the border of duplex region for unwinding. For example, in the presence of a DNA polymerase, *E. coli* DnaB helicase unwinds DNA at a rate of 750 bp/sec with a processivity greater than 50 kb and T7 gp4 helicase unwinds DNA at a rate of 300 bp/sec with high processivity (Kornberg and Baker, supra (1992)). SV40 large T antigen unwinds DNA at a rate of 75 to 100 bp/sec with high processivity (Kornberg and Baker, supra (1992); Li et al., *Nature*. 423:512–518 (2003)).

While not wishing to be bound by theory, it is possible that although some helicases, such as T7 Gp4, prefer duplex DNA with single-stranded tails, they may still have low unwinding activity on blunt-end duplex DNA molecules. It is also possible that single-stranded tails may be transiently present at the border of a duplex DNA through "terminal breathing" of the duplex DNA molecule (Roychoudhury et al., *Nucleic acid Res*. 6:1323–3123 (1979)). These transient single-stranded tails may be captured by the T7 helicase, which then continues the unwinding process.

Regardless of the source of the target nucleic acid, a helicase preparation may be used to replace a heat denaturation step during amplification of a nucleic acid by unwinding a double stranded molecule to produce a single stranded molecule for polymerase dependent amplification without a change in temperature of reaction. Hence thermocycling that is required during standard PCR amplification using Taq polymerase may be avoided.

In general, the temperature of denaturation suitable for permitting specificity of primer-template recognition and subsequent annealing may occur over a range of temperatures, for example 20° C.–75° C. A preferred denaturation temperature may be selected according to which helicase is selected for the melting process. Tests to determine optimum temperatures for amplification of a nucleic acid in the presence of a selected helicase can be determined by routine experimentation by varying the temperature of the reaction mixture and comparing amplification products using gel electrophoresis.

Denaturation of nucleic acid duplexes can be accelerated by using a thermostable helicase preparation under incubation conditions that include higher temperature for example in a range of 45° C.–75° C. (Example XII). Performing HDA at high temperature using a thermostable helicase preparation and a thermostable polymerase may increase the specificity of primer binding which can improve the specificity of amplification.

In certain circumstances, it may be desirable to utilize a plurality of different helicase enzymes in an amplification reaction. The use of a plurality of helicases may enhance the yield and length of target amplification in HDA under certain conditions where different helicases coordinate various functions to increase the efficiency of the unwinding of duplex nucleic acids. For example, a helicase that has low processivity but is able to melt blunt-ended DNA may be combined with a second helicase that has great processivity but recognizes single-stranded tails at the border of duplex region for the initiation of unwinding (Example X). In this example, the first helicase initially separates the blunt ends of a long nucleic acid duplex generating 5' and 3' single-stranded tails and then dissociates from that substrate due to its limited processivity. This partially unwound substrate is subsequently recognized by the second helicase that then continues the unwinding process with superior processivity. In this way, a long target in a nucleic acid duplex may be unwound by the use of a helicase preparation containing a plurality of helicases and subsequently amplified in a HDA reaction.

Primers

Generally, primer pairs suitable for use in HDA are short synthetic oligonucleotides, for example, having a length of more than 10 nucleotides and less than 50 nucleotides. Oligonucleotide primer design involves various parameters such as string-based alignment scores, melting temperature, primer length and GC content (Kampke et al., *Bioinformatics* 17:214–225 (2003)). When designing a primer, one of the important factors is to choose a sequence within the target fragment which is specific to the nucleic acid molecule to be amplified. The other important factor is to decide the melting temperature of a primer for HDA reaction. The melting temperature of a primer is determined by the length and GC content of that oligonucleotide. Preferably the melting temperature of a primer is should about 10 to 30° C. higher than the temperature at which the hybridization and amplification will take place. For example, if the temperature of the hybridization and amplification is set at 37° C. when using the E. coli UvrD helicase preparation, the melting temperature of a pair of primers designed for this reaction should be in a range between about 47° C. to 67° C. If the temperature of the hybridization and amplification is 60° C., the melting temperature of a pair of primers designed for that reaction should be in a range between 65° C. and 90° C. To choose the best primer for a HDA reaction, a set of primers with various melting temperatures can be tested in a parallel assays. More information regarding primer design is described by Kampke et al., *Bioinformatics* 17:214–225 (2003).

Each primer hybridizes to each end of the target nucleic acid and may be extended in a 3' to 5' direction by a polymerase using the target nucleotide sequence as a template (FIG. 3). Conditions of hybridization are standard as described in "Molecular Cloning and Laboratory Manual" $2^{nd}$ ed. Sambrook, Rich and Maniatis, pub. Cold Spring Harbor (2003). To achieve specific amplification, a homologous or perfect match primer is preferred. However, primers may include sequences at the 5' end which are non complementary to the target nucleotide sequence(s). Alternatively, primers may contain nucleotides or sequences throughout that are not exactly complementary to the target nucleic acid. Primers may represent analogous primers or may be non-specific or universal primers for use in HDA as long as specific hybridization can be achieved by the primer-template binding at a predetermined temperature.

The primers may include any of the deoxyribonucleotide bases A, T, G or C and/or one or more ribonucleotide bases, A, C, U, G and/or one or more modified nucleotide (deoxyribonucleotide or ribonucleotide) wherein the modification does not prevent hybridization of the primer to the nucleic acid or elongation of the primer or denaturation of double stranded molecules. Primers may be modified with chemical groups such as phosphorothioates or methylphosphonates or with non nucleotide linkers to enhance their performance or to facilitate the characterization of amplification products.

To detect amplified products, the primers may be subject to modification, such as fluorescent or chemiluminescent-labeling, and biotinylation. (for example, fluorescent tags such as amine reactive fluorescein ester of carboxyfluorescein-Glen Research, Sterling, Va.). Other labeling methods include radioactive isotopes, chromophores and ligands such as biotin or haptens which while not directly detectable can be readily detected by reaction with labeled forms of their specific binding partners eg avidin and antibodies respectively.

Primers as described herein can be prepared by methods known in the art. (see, for example U.S. Pat. No. 6,214,587).

In embodiments, a pair of two sequence-specific primers, one hybridizing to the 5'-border of the target sequence and the other hybridizing to the 3'-border of the target (FIG. 3), are used in HDA to achieve exponential amplification of a target sequence. This approach can be readily distinguished from Lee et al. (*J. Mol. Biol.* 316:19–34 (2002)). Multiple pairs of primers can be utilized in a single HDA reaction for amplifying multiple targets simultaneously using different detection tags in a multiplex reaction. Multiplexing is commonly used in SNP analysis and in detecting pathogens (Jessing et al., *J. Clin. Microbiol.* 41:4095–4100 (2003)).

Polymerases

Polymerases are selected for HDA on the basis of processivity and strand displacement activity. Subsequent to melting and hybridization with a primer, the nucleic acid is subjected to a polymerization step. A DNA polymerase is selected if the nucleic acid to be amplified is DNA. When the initial target is RNA, a reverse transcriptase is used first to copy the RNA target into a cDNA molecule and the cDNA is then further amplified in HDA by a selected DNA polymerase (Example VII). The DNA polymerase acts on the target nucleic acid to extend the primers hybridized to the nucleic acid templates in the presence of four dNTPs to form primer extension products complementary to the nucleotide sequence on the nucleic acid template (FIG. 1 and FIG. 3).

The DNA polymerase is selected from a group of polymerases lacking 5' to 3' exonuclease activity and which additionally may optionally lack 3'-5' exonuclease activity.

Examples of suitable DNA polymerases include an exonuclease-deficient Klenow fragment of E. coli DNA polymerase I (New England Biolabs, Inc. (Beverly, Mass.)), an exonuclease deficient T7 DNA polymerase (Sequenase; USB, (Cleveland, Ohio)), Klenow fragment of E. coli DNA polymerase I (New England Biolabs, Inc. (Beverly, Mass.)), Large fragment of Bst DNA polymerase (New England Biolabs, Inc. (Beverly, Mass.)), KlenTaq DNA polymerase (AB Peptides, (St Louis, Mo.)), T5 DNA polymerase (U.S. Pat. No. 5,716,819), and Pol III DNA polymerase (U.S. Pat. No. 6,555,349). DNA polymerases possessing strand-displacement activity, such as the exonuclease-deficient Klenow fragment of E. coli DNA polymerase I, Bst DNA polymerase Large fragment, and Sequenase, are preferred for Helicase-Dependent Amplification. T7 polymerase is a high fidelity polymerase having an error rate of $3.5 \times 10^5$ which is significantly less than Taq polymerase (Keohavong and Thilly, *Proc. Natl. Acad. Sci. USA* 86, 9253–9257 (1989)). T7 polymerase is not thermostable however and therefore is not optimal for use in amplification systems that require thermocycling. In HDA, which can be conducted isothermally, T7 Sequenase is a one of the preferred polymerases for amplification of DNA.

Single-stranded DNA Binding Proteins

Helicases show improved activity in the presence of single-strand binding proteins (SSB). In these circumstances, the choice of SSB is generally not limited to a specific protein. Examples of single strand binding proteins are T4 gene 32 protein, E. coli SSB, T7 gp2.5 SSB, phage phi29 SSB (Kornberg and Baker, supra (1992)) and truncated forms of the aforementioned.

Other Chemical Reagents

In addition to salt and pH, other chemical reagents, such as denaturation reagents including urea and dimethyl-sulfoxide (DMSO) can be added to the HDA reaction to partially denature or de-stabilize the duplex DNA. HDA reactions can be compared in different concentrations of denaturation reagents with or without SSB protein. In this way, chemical compounds can be identified which increase HDA efficiency and/or substitute for SSB in single-strand (ss) DNA stabilization. Most of the biomacromolecules such as nucleic acids and proteins are designed to function and/or form their native structures in a living cell at much high concentrations than in vitro experimental conditions. Polyethylene glycol (PEG) has been used to create an artificial molecular crowding condition by excluding water and creating electrostatic interaction with solute polycations (Miyoshi, et al., *Biochemistry* 41:15017–15024 (2002)). When PEG (7.5%) is added to a DNA ligation reaction, the reaction time is reduced to 5 min (Quick Ligation Kit, New England Biolabs, Inc. (Beverly, Mass.)). PEG has also been added into helicase unwinding assays to increase the efficiency of the reaction (Dong, et al., *Proc. Natl. Acad. Sci. USA* 93:14456–14461 (1996)). PEG or other molecular crowding reagents on HDA may increase the effective concentrations of enzymes and nucleic acids in HDA reaction and thus reduce the reaction time and amount of protein concentration needed for the reaction.

Cofactors

ATP or TTP is a commonly preferred energy source for highly processive helicases. On average one ATP molecule is consumed by a DNA helicases to unwind 1 to 4 base pairs (Kornberg and Baker, supra (1992)). In an embodiment of the invention, the UvrD-based HDA system had an optimal initial ATP concentration of 3 mM. To amplify a longer target, more ATP may be consumed as compared to a shorter target. In these circumstances, it may be desirable to include a pyruvate kinase-based ATP regenerating system for use with the helicase (Harmon and Kowalczykowski, *Journal of Biological Chemistry* 276:232–243 (2001)).

Topoisomerase

Topoisomerase can be used in long HDA reactions to increase the ability of HDA to amplify long target amplicons. When a very long linear DNA duplex is separated by a helicase, the swivel (relaxing) function of a topoisomerase removes the twist and prevents over-winding (Kornberg and Baker, supra (1992)). For example, *E. coli* topoisomerase I (Fermentas, Vilnius, Lithuania) can be used to relax negatively supercoiled DNA by introducing a nick into one DNA strand. In contrast, *E. coli* DNA gyrase (topoisomerase II) introduces a transient double-stranded break into DNA allowing DNA strands to pass through one another (Kornberg and Baker, supra (1992)).

Detection of Amplified Nucleic Acids

Amplified nucleic acid product may be detected by various methods including ethidium-bromide staining and detecting the amplified sequence by means of a label selected from the group consisting of a radiolabel, a fluorescent-label, and an enzyme. For example HDA amplified products can be detected in real-time using fluorescent-labeled LUX™ Primers (Invitrogen Corporation, Carlsbad, Calif.) which are oligonucleotides designed with a fluorophore close to the 3' end in a hairpin structure. This configuration intrinsically renders fluorescence quenching capability without separate quenching moiety. When the primer becomes incorporated into double-stranded amplification product, the fluorophore is dequenched, resulting in a significant increase in fluorescent signal. Example XIV demonstrates real-time detection of a target sequence using fluorescent-labeled primers and the HDA method.

Identifying a Helicase which can be Used in HDA

To test whether a helicase can be used in the HDA reaction to amplify a target nucleic acid, a HDA reaction can be set up as following:

(a) a short double stranded oligonucleotide (less than 100 nucleotides) can be used as the substrate for amplification. Primers are prepared which can hybridize to the 5' and 3' ends of the oligonucleotide. The double-stranded oligonucleotide is denatured to form single strands in a first mixture of the primers in a standard Tris acetate buffer (10 mM, pH 7.5) or ThermoPol (New England Biolabs, Inc. (Beverly, Mass.)) buffer and varying amounts of dNTPs or NTPs. The mixture is heated to 95° C. for 10 minutes, 53° C. for 1 minute.

(b) a second mixture is prepared where the second mixture has a concentration of the helicase to be tested in a HDA buffer with a pH which is varied between pH6.0 and pH9.0. The standard buffer may have a concentration of NaCl and KCl, each in a concentration range of about 0–200 mM. The concentration of the helicase is also varied. A single stranded binding protein such as T4gp 32 is added together with a DNA polymerase and 4 dNTPs in a standard amount for use in an amplification reaction which additionally includes a nucleic acid to be amplified and primers.

(c) the mixtures are combined and incubated for 2 hours at 37° C. (or at a temperature and then analyzed on a 3% GPG LMP agarose gel.

By performing repeated reactions under the different conditions described above, the optimal conditions for HDA can be determined for a particular helicase.

The helicase can then be tested for its ability to amplify plasmid DNA, longer DNA molecules and for amplifying short sequence in genomic DNA as illustrated in the Examples for *E. coli* UvrD helicases.

Helicase dependent amplification is here demonstrated to be an improved method of nucleic acid amplification for use in a wide variety of applications. These include amplification following reverse transcription and quantitative amplification using real time HDA. The Examples below illustrate how HDA is a sensitive and effective method for amplifying nucleic acids having a wide range of sizes. One measure of the sensitivity of the HDA reaction is its capacity to amplify a nucleic acid sequences in the range of 10 fold to over 1 billion fold.

Table 1 contains some sample values although these are not intended to be limiting.

TABLE 1

| | Amplification rates | | |
|---|---|---|---|
| Substrate | Starting Amount | End Amount | Fold of Amplification |
| Oligo | 5 ng | 500 ng | 100 |
| Plasmid | 25 ng of 2700 bp | 500 ng of 100 bp | 5000 |
| Genomic DNA | 100 ng of 3 Mb | 300 ng of 100 bp | $1 \times 10^5$ |
| Genomic DNA | 0.1 ng of 3 Mb | 300 ng of 100 bp | $1 \times 10^9$ |

Amplification Conditions—Temperature

Although other isothermal nucleic acid amplification methods such as Strand-Displacement Amplification can amplify target at a constant temperature without thermocycling, they do require an initial denaturation step to generate single-stranded template. An advantage of embodiments of the method is that both unwinding by helicase and amplification can effectively occur at a single temperature throughout as demonstrated in Example IX Alternatively, the temperature is raised to assist initial unwinding of the target nucleic acid by the helicase and the amplification then proceeds at a single temperature.

We have shown that HDA can be used in place of PCR for amplification of reverse transcribed product of RNA (Example VII). In addition, HDA is expected to be useful for quantitative amplification such as found to be useful in gene expression studies and environmental analyses. Accordingly, where it is desirable to determine the amounts of a target nucleic acid, HDA can be utilized in a real time end point assay. Accordingly, HDA may be used to determine the relative amounts of messenger RNA in a cell in gene expression studies. For example, calibrated gene expression profiles described in WO 0125473 can be generated using quantitative helicase dependent amplification or Q-HDA.

Real time HDA may be used as a sensitive technique to determine amounts of an organism in a contaminated sample such as *E. coli* in seawater. Real time detection using sensitive markers such as fluorescence in a HDA reaction has been demonstrated in Example XIV.

HDA may be developed in the context of a compact device for use in field activities and/or laboratory diagnoses. For example, HDA could be practiced in a microfluidic environment. Microfluidics technologies (lab on a chip) are rapidly emerging as key strategies for cost and time saving by performing biochemical analyses in miniaturized environment usually at nanoliter scale. Microfluidics technologies have great potential to be used as field-portable equipment in pathogen detection when combining with a nucleic acid amplification and detection method. The ability of HDA to amplify nucleic acids in an isothermal condition without initial heat-denaturation makes it a good candidate for the nucleic acid amplification process in a microfluidic device. Similarly, HDA may be used either in kits or in laboratory amplification procedures to create response profiles of the sort described in International Publication No. WO 0202740 or for monitoring disease (U.S. Publication No. 2001018182).

Examples II–XIV illustrate that HDA is effective for amplifying target nucleic acid from different sources and having different sequences. Examples IV describe amplification of various lengths of target sequences from DNA plasmids using HDA. Examples X demonstrates that longer target sequence (>2 kb) can be amplified by the T7 Gp4B-based HDA system. Examples X further demonstrates that the method of using Helicase-Dependent Amplification to amplify nucleic acids can be performed using different helicase preparations, such as a helicase preparation containing T7 Gp4B helicase, or a helicase preparation containing more than one helicase, such as T7 Gp4B helicase and UvrD helicase.

The demonstration in Example VIII that amplification of merely 10 copies of bacterial genomic DNA can be successfully achieved using HDA, supports the use of HDA for molecular diagnostics application of infectious diseases caused by pathogenic bacteria, for example *Chlamydia trachomatis* and *Neisseria gonorrhoeae*. The demonstration that target sequences can be amplified from human genomic DNA samples (Example VI) supports the use of HDA in identifying genetic alleles corresponding to a particular disease including single nucleotide polymorphisms and forensic applications that rely on characterizing small amounts of nucleic acid at the scene of a crime or at an archeological site.

The following Examples are provided to aid in the understanding of the invention and are not construed as a limitation thereof.

The references cited above and below are herein incorporated by reference.

EXAMPLE I

Cloning and Purifying UvrD Helicase and its Accessory Protein MutL

1. Cloning the Genes Encoding UvrD Helicase and MutL Protein

Genes encoding *E. coli* helicase II or UvrD helicase (Swissprot Accession No.: P03018) and its accessory protein *E. coli* MutL protein (Swissprot Accession No.: P23367) were cloned using the Impact™ system which leads to a C-terminal translational fusion of a bifunctional tag consisting of the *S. cerevisiae* VMA intein and a chitin-binding domain (New England Biolabs, Inc. (Beverly, Mass.)). This protein purification system utilizes the DTT-inducible self-cleavage activity of a protein splicing element (termed an intein) to separate the target protein from the affinity tag (chitin binding domain). Vent® DNA polymerase was used to amplify UvrD gene from *E. coli* K12 genomic DNA using primer 5A (5' GGTGGTACCATGGACGTTTCT TACCT-GCTC 3' (SEQ ID NO:1)) and primer 3A (5' GGTGGTGCT CTTCCGCACACCGACTCCA GCCGGGC 3' (SEQ ID NO:2)). The mutL gene was amplified from *E. coli* K12 genomic DNA using primer 5B (5' GGTGGTCATATGCCA ATTCAGGTCTTACCG 3' (SEQ ID NO:3)) and primer 3B (5' GGTGGTTGCTCTTCCGCACTCA TCTTTCAGGGCTTTTATC 3' (SEQ ID NO:4)). *E. Coli* K-12 was obtained from New England Biolabs, Inc. (Beverly, Mass.). The genomic DNA was isolated with the Qiagen genomic DNA kit (Qiagen, Hilden (Germany)). The primers contained restriction enzymes sites that allowing the cloning of the mutL gene into the NdeI and SapI sites of pTYB1 (New England Biolabs, Inc., (Beverly, Mass.)) and the uvrD gene into the NcoI and SapI sites of pTYB3 (New England Biolabs, Inc., (Beverly, Mass.)). Ligation products were transformed into ER2502 cells. Positive transformants were screened by selective growth on LB plates containing 100 μl/ml ampicillin, followed by colony PCR and sequencing of the insert. After analysis of sequencing results, correct constructs were transformed into *E. coli* ER2566 cells. ER2566 cells containing either pTYB1-MutL or pTYB3-UvrD were grown at 37° C. in LB media supplemented with 100 ug/ml ampicillin. When $OD_{550}$ reached ~0.5, protein expression was induced with 0.5 mM isopropyl-β-D-thiogalactopyranoside (IPTG). After an overnight incubation at 15° C., cells were harvested by centrifugation.

2. UvrD and MutL Purification

The chitin binding domain (CBD) of the intein tag allowed affinity purification of the fusion proteins on a chitin bead column (New England Biolabs, Inc., (Beverly, Mass.)). All procedures were performed at 4° C. Cells expressing UvrD from a 6 liter culture were resuspended in 210 ml sonication buffer (20 mM Tris pH 7.8, 0.1 mM EDTA, 50 mM NaCl, 20 μM PMSF, 5% glycerol) and were broken by sonication. The clarified extract was loaded on a 45-ml chitin bead column pre-equilibrated with 500 ml of buffer A (20 mM Tris-HCl (pH 8), 1 mM EDTA) plus 500 mM NaCl. The column was washed with 500 ml of buffer A plus 1 M NaCl and 500 ml of buffer A plus 500 mM NaCl. Induction of self-cleavage was conducted by flushing the column with 3 column volumes (135 ml) of cleavage buffer (buffer A+500 mM NaCl+50 mM dithiothreitol (DTT)). The cleavage reaction was carried out at 4° C. for 64 hours in cleavage buffer. The protein was eluted with 67 ml of buffer B (20 mM Tris-HCl (pH 8), 1 mM EDTA, 1 mM DTT) plus 50 mM NaCl. The positive fractions were pooled and loaded on a 1 ml-MonoQ column (Pharmacia (Piscataway, N.J.)) which had been pre-equilibrated with buffer B plus 50 mM NaCl. The flow-through and eluted fractions were analyzed on SDS-PAGE. Helicase activities in positive fractions were further tested by measuring the ability of the helicase to displace a fluorescent-labeled oligonucleotide (30-nucleotide, (nt)) from a partial duplex, which was prepared by annealing the 30-nt oligonucleotide to a complementary non-labeled 70-nt oligonucleotide. The displaced 30-nt labeled oligonucleotide was trapped by another non-label 30-nt complementary oligonucleotide. The oligonucleotides were separated by electrophoresis in a 20% non-denaturing polyacrylamide gel and the displaced oligonucleotides were visualized by UV light. UvrD protein and helicase activity were found in the flow-through and the wash fractions. These fractions were mixed and then loaded on a 1-ml Heparin TSK column (Pharmacia (Piscataway, N.J.)). Again, UvrD didn't bind to the column. A one-ml hydroxylapatite column (TosoHaas (Philadelphia, Pa.)) retained UvrD, which eluted at around 340 mM NaCl in a linear gradient (50 mM–1 M NaCl). The pure fractions were pooled and dialyzed overnight against storage buffer (20 mM Tris-HCl (pH8.2), 200 mM NaCl, 1 mM EDTA, 1 mM EGTA, 15 mM 2-mercaptoethanol, 50% glycerol). The final concentration was determined using the Bradford protein assay (Bradford, *Anal. Biochem.* 72:248–254 (1976)) and SDS polyacrylamide gel electrophoresis (SDS-PAGE).

MutL was purified similarly to UvrD. A 6-liter culture of ER2566/pTYB1-MutL was used. All procedures were performed at 4° C. The chitin bead column purification conditions were similar to the UvrD except that column volume was 14 ml. The column was washed with 125 ml of buffer A plus 1 M NaCl and 125 ml of buffer A plus 500 mM NaCl. Induction of self-cleavage was conducted by flushing the column with 45 ml of cleavage buffer (buffer A+500 mM NaCl+50 mM DTT). The cleavage reaction was carried out at 4° C. for 40 hours in cleavage buffer. The protein was eluted with 36-ml of buffer B+50 mM NaCl. The positive fractions were pooled and loaded on a 1-ml MonoQ column. MutL was found in the flow through of the column. The flow-through and the washing fractions were thus pooled and dialyzed against buffer B+40 mM NaCl to get a final NaCl concentration of 50 mM. The sample was loaded on a 1-ml Heparin TSK column. MutL was retained, eluting at 565 mM NaCl. However other protein bands could be detected on SDS-PAGE and an exonuclease assay showed that exonuclease activity was present in the fractions of interest. These fractions were pooled and dialyzed against buffer B+50 mM NaCl. The 1-ml MonoQ column was used a second time to separate MutL from contaminant proteins. MutL eluted at 220 mM NaCl. The pure fractions were pooled and concentrated by a Centriplus YM 10 (Millipore, (Bedford Mass.)) before being dialyzed overnight against the storage buffer (25 mM Tris-HCl (pH 7.5), 200 mM NaCl, 1 mM 2-mercaptoethanol, 0.1 mM EDTA, 50% glycerol). The final concentration was determined using the Bradford protein assay and polyacrylamide gel electrophoresis (PAGE).

3. Other Cloning and Purification Systems

In addition to Impact™, helicases and their accessory proteins may be purified using several alternative methods such as direct cloning (cloning the gene into a vector without an additional tag), His-Tag® (Novagen, Inc. (Madison, Wis.)), and PMAL™ protein fusion & purification system (New England Biolabs, Inc. (Beverly, Mass.)). The *E. coli* UvrD helicase was cloned into plasmid pET15b (Novagen, Inc. (Madison, Wis.)) and pMAL-c2X (New England Biolabs, Inc. (Beverly, Mass.)). The His-Tag fusion, UvrD-His, was purified using a His.Bind® column and a protocol provided by the manufactory (Novagen, Inc. (Madison, Wis.)). The UvrD-His protein was further purified by a hydroxylapatite column. The MBP-UvrD fusion protein was purified using an amylose column and a protocol provided by the manufactor (New England Biolabs, Inc., (Beverly, Mass.)). Both UvrD-His protein and MBP-UvrD fusion protein showed functional unwinding activity and could be used in a Helicase-Dependent Amplification reaction.

EXAMPLE II

Method of Amplification of a Nucleic Acid Duplex Target

As a model system for Helicase Dependent Amplification, a synthetic DNA duplex was used as template in the HDA reaction. This example illustrates amplification of this DNA duplex using the UvrD HDA system. A method for template denaturation, primer annealing and extension is described below.

Figure 2A:
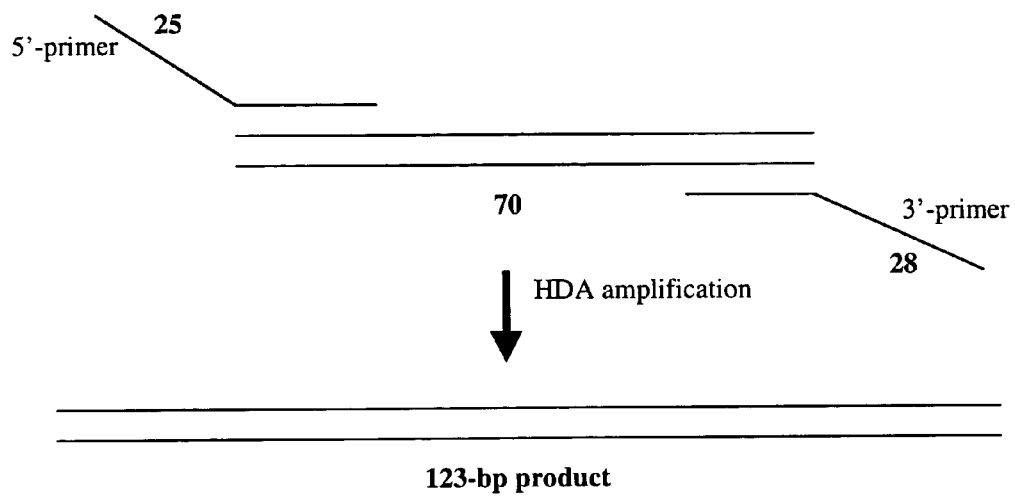
FIG. 2A. Schematic presentation of HDA amplification of an oligonucleotide with primers for producing an amplified product.
Figure 2B:
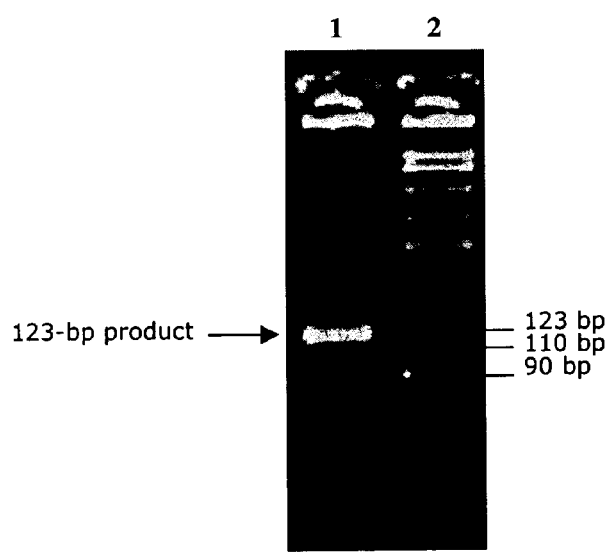
FIG. 2B. An HDA reaction according to FIG. 2A in which the HDA product is characterized on a 3% LMP agarose gel (Lane 1) and Lane 2 contains the pBR322/MspI ladder used as size marker (M).

Thirty five μl of reaction Component A was made by mixing 10 μl of 5×HDA Buffer A (175 mM Tris-HCl (pH7.5), 5 mM DTT), 0.5 μl of 70-bp DNA template derived from top oligodeoxy-nucleotides (2 μM; 5' TGGCTGGT-CACCAGAGGGTGGCGCGGAC CGAGTGCGCTCG-GCGGCTGCGGAGAGGGGTAGAGCAGGCAGC 3' (SEQ ID NO:5)) and bottom oligodeoxynucleotides (2 μM; 5' GCTGCCTGCTCTACCCCTCTCCGCAGC-CGCCGAGCGCACTCGGTC CGCGCCACCCTCTGGT-GACCAGCCA 3' (SEQ ID NO:6)), 1 μl of 5'-primer (10 μM; 5' CATGTTAGGTTCTATGGATCGAGTCTGGCTGG TCACCAGAGGG 3' (SEQ ID NO:7)), 1 μl of 3'-primer (10 μM; 5' TCCCTTAGAGGTCACATTGGATC-GAGTCGCTGCCTGCTCTACCCC 3' SEQ ID NO:8)), 10 μl of four dNTPs (2 mM each), 1.5 μl ATP (100 mM), and 11 μl dH$_2$O. The reaction Component A was heated for 2 min at 95° C. to denature the template, 3 min at 53° C. to anneal primers and 2 min at 37° C. before adding 0.5 μl of MutL protein (800 ng/μl). Fifteen μl of reaction Component B was prepared by mixing 10 μl 5×HDA buffer B (5 mM Tris-Cl (pH7.9), 25 mM NaCl, 55 mM MgCl$_2$2, 0.5 mg/ml BSA, 0.5 mM DTT), 0.5 μl exo⁻ Klenow Fragment of *E. coli* DNA polymerase I (5 units/μl), 0.5 μl UvrD helicase (200 ng/μl), 0.9 μl T4 gene 32 protein (gp32; 5 μg/μl), and 3.1 μl dH$_2$O, and was then added to the Component A following the addition of MutL. The exo⁻ Klenow Fragment is commercially available (New England Biolabs, Inc., (Beverly, Mass.)) and T4 gene 32 protein is also commercially available (Roche Applied Science, (Indianapolis, Ind.)). The reaction continued for 30 minutes at 37° C. and was then terminated by addition of 12.5 μl stop-buffer (1% SDS, 0.05 M EDTA, 30% glycerol, 0.2% Bromophenol blue). Reaction products were analyzed on a 3% Genomic Performance Grade (GPG) low-melting-point (LMP) agarose gel (American Bioanalytical (Natick, Mass.)) in Tris Borate EDTA (TBE) buffer and ethidium bromide (FIG. 2B). A DNA fragment about of 120 bp was observed (FIG. 2B), which matched the predicted product size of 123 bp (FIG. 2A).

EXAMPLE III

Amplication of a Specific Sequence from Plasmid DNA by HDA

To test whether HDA can be used to amplify a specific target sequence from a DNA template, we used two pUC19/M13 universal primers, primer-1224 and primer-1233, to amplify a 110-bp sequence from a 2647-bp DNA plasmid, pAH1 (FIG. 15 (SEQ ID NO:9)) using the UvrD HDA system. Primer-1224 and primer-1233 are commercially available and their sequence can be obtained at the company (New England Biolabs, Inc., (Beverly, Mass.)). The amplification scheme is outlined in FIG. 3.

Two acetate-based reaction buffers were pre-made: 10×HDA Buffer A contains 350 mM Tris-Acetate (pH7.5) and 100 mM DTT; 10×HDA Buffer B contains 10 mM Tris-Acetate (pH7.5), 1 mg/ml BSA, and 90 mM Magnesium Acetate. The HDA reaction Component A was set up by combining:
5 µl 10×HDA Buffer A
1.5 µl of 23 nM AhdI-cleaved pAH1 plasmid
1 µl of 10 µM primer-1224
1 µl of 10 µM primer-1233
2 µl dNTPs (10 mM)
1.5 µl ATP (100 mM)
8 µl dH$_2$O The reaction Component A was heated for 2 min at 95° C. to denature the template, 3 min at 69° C. to anneal primers and 2 min at 37° C. before adding Component B.

Figure 4:
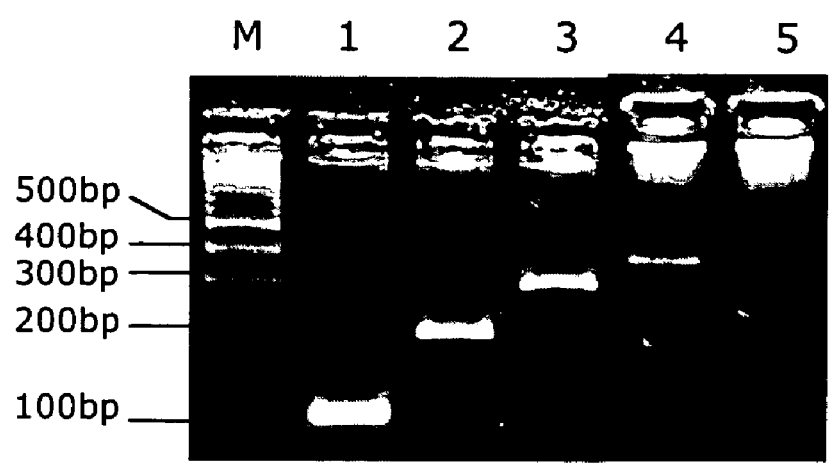
FIG. 4. Amplification of target sequences of various sizes from DNA plasmids.

Fifteen µl of reaction Component B was prepared by mixing:
5 µl 10×HDA Buffer B
1 µl exo⁻ Klenow Fragment (5 units/µl)
0.5 µl UvrD helicase (200 ng/µl)
1 µl MutL protein (400 ng/µl)
0.9 µl T4 gp32 (5 µg/µl)
21.6 µl dH$_2$O Component B was then added to the Component A. The reaction was continued for one more hour at 37° C. and was then terminated by addition of 12.5 µl stop-buffer (1% SDS, 0.05 M EDTA, 30% glycerol, 0.2% Bromophenol blue). Reaction products were analyzed on a 2% GPG LMP gel containing ethidium bromide (FIG. 4).

A 110-bp amplification product was observed on the 2% agarose gel. The size of this product matched the predicted length of the target sequence (FIG. 4, lane 1). In the absence of UvrD helicase, no amplification was observed confirming that helicase is required for the amplification. Moreover, the results indicated that UvrD was substantially more effective at amplifying target DNA in the presence of MutL and T4Gp32 SSB.

EXAMPLE IV

Method of Amplification of Various Target Sequences from DNA Plasmids

To test whether the UvrD based HDA system was capable to amplify various target sequences, several parallel reactions were carried out using pAH1-derived plasmids containing different sequences and sizes of inserts between primer 1224 and primer 1233.

A 50 µl HDA reaction was set up using two reaction Components, A and B, described below and mixing them in a sequential order. Two acetate-based reaction buffers were pre-made: 10×HDA Buffer A contains 350 mM Tris-Acetate (pH7.5) and 100 mM DTT; 10×HDA Buffer B contains 10 mM Tris-Acetate (pH7.5), 1 mg/ml BSA, and 100 mM Magnesium Acetate.

Thirty five µl of Component A was made by combining:
5 µl 10×HDA Buffer A
1 µl pAH1 plasmid or pAH1 derivatives (50 ng/µl)
1 µl of 10 µM primer-1224
1 µl of 10 µM primer-1233
10 µl dNTPs (2 mM)
1.5 µl ATP (100 mM)
15.5 µl dH$_2$O Fifteen µl of reaction Component B was prepared by mixing:
5 µl 10×HDA Buffer B
1 µl exo⁻ Klenow Fragment (5 units/µl)
0.5 µl UvrD helicase (200 ng/µl)
0.5 µl MutL (800 ng/µl)
0.9 µl T4 gp32 (5 µg/µl)
7.1 µl dH$_2$O The HDA reaction was started by heating Component A at 95° C. for 2 min to denature the template. The Component A was then incubated for 3 min at 69° C. to anneal primers and 2 min at 37° C. to cool down the reaction. Fifteen µl of freshly made Component B was added to 35 µl Component A following the denaturation, annealing, and cooling steps. The reaction continued for one more hour at 37° C. and was then terminated upon addition of 12.5 µl stop-buffer (1% SDS, 0.05 M EDTA, 30% glycerol, 0.2% Bromophenol blue). Amplification products were visualized on a 3% GPG LMP agarose gel in TBE buffer and ethidium bromide (FIG. 4). All of the amplification products matched the predicted target sizes (FIG. 4, lanes 1–5). In addition, the UvrD-based HDA system was able to amplify a target DNA as large as 650 bp in a HDA reaction (FIG. 4, lane 5).

EXAMPLE V

Amplication of a Specific Sequence from Bacterial Genomic DNA by HDA

HDA can also be used to amplify a specific target sequence from more complicated nucleic acid samples, such as viral genomic DNA or RNA, bacterial genomic DNA or human genomic DNA. In this example, we disclose a method to amplify and detect a specific target sequence from a bacterial genome of an oral pathogen, *Treponema denticola* ATCC No. 35405, using the *E. coli* UvrD-based HDA system. A restriction endonuclease gene earIR was chosen as the target gene (FIG. 16 (SEQ ID NO:10)), and one 5'-primer and two 3'-primers were designed to hybridize to the sequence of earIR gene. The reaction buffers and protocol were modified for genomic DNA amplification. 10×HDA Buffer A contains 350 mM Tris-Acetate (pH7.5) and 100 mM DTT. 10×HDA Buffer B contains 10 mM Tris-Acetate (pH7.5), 1 mg/ml BSA, and 100 mM Magnesium Acetate.

The 20 µl Component A was set up by combining:
5 µl 10×HDA Buffer A
2 µl of *Treponema denticola* genomic DNA (50 ng/µl)
2 µl of 10 µM primer-58861 (5' CCAAATGATGCTTATG TTGCTT 3' (SEQ ID NO:11))
2 µl of 10 µM primer-58862 (5' CATAAGCCTCTCTTG-GAT CT 3' (SEQ ID NO:12))
or 2 µl of 10 µM primer-58863 (5' TCCACATCTTTCA-CAT TTCCAT 3' (SEQ ID NO:13)
2 µl dNTPs (10 mM)
7 µl dH$_2$O Thirty µl of reaction Component B was prepared by mixing:
5 µl 10×HDA Buffer B
4 µl 100 mM ATP
0.5 µl UvrD helicase (200 ng/µl)
0.5 µl MutL (800 ng/µl)
0.9 µl T4 gp32 (5 µg/lµl)
1 µl exo⁻ Klenow Fragment (5 units/µl)
18.1 µl dH$_2$O The reaction Component A was heated for 10 min at 95° C., 1 min at 53° C., and 2 min at 37° C. The freshly made Component B was then added to Component A after it cooled down to 37° C. The reaction was continued for two more hours at 37° C. and was then terminated by addition of 12.5 µl stop-buffer. Reaction products were analyzed on a 3% GPG LMP agarose gel (FIG. 5A). The predicted size of the target DNA is 97 bp between primer-58861 and primer- 58862 (FIG. 5A, lane 1), and the predicted length between primer-58861 and primer-58863 is 129 bp (FIG. 5A, lane 2). Two products were observed on an agarose gel and both matched the predicted sizes of the target DNA. The amplification products were sequenced and the sequencing results confirmed that both match the sequence of the target DNA.

To test whether the UvrD helicase preparation can work with different DNA polymerases, the HDA reaction was carried out to amplify the 129-bp target sequence from *T. denticola* genome using UvrD helicase preparation and T7 Sequenase (USB, (Cleveland, Ohio)).

The reaction Component A (20 µl ) was prepared by mixing:
5 µl 10×HDA Buffer A
2 µl of *Treponema denticola* genomic DNA (50 ng/µl)
2 µl of 10 µM primer-58861 (5' CCAAATGATGCTTA TGTTGCTT 3' (SEQ ID NO:11))
2 µl of 10 µM primer-58863 (5' TCCACATCTTTCACAT TTCCAT 3' (SEQ ID NO:13))
2 µl dNTPs (10 mM)
7 µl dH$_2$O Thirty µl of reaction Component B was prepared by mixing:
5 µl 10×HDA Buffer B
4 µl 100 mM ATP
0.5 µl UvrD helicase (200 ng/µl)
0.5 µl MutL (800 ng/µl)
0.9 µl T4 gp32 (5 µg/µl)
1 µl T7 Sequenase (1.5 units/µl or 3.5 units/µl)
18.1 µl dH$_2$O The HDA reaction was carried out same as described above. Reaction products were analyzed on a 3% GPG LMP agarose gel (FIG. 5B). An amplified product around 130 bp was observed on an agarose gel and it matched the predicted sizes of the target sequence of 129 bp (FIG. 5B, lanes 1 and 2).

EXAMPLE VI

Amplifying Target Sequence from Human Genomic DNA Samples by HDA

In this example, we disclose a method to amplify a target sequence from human genomic DNA sample using the *E. coli* UvrD-based HDA system. Human genomic DNA prepared from a breast cancer cell line was purchased from ATCC No. 45537. Two primers, which are specific to the human DNA methyltransferase gene (dnmt1), were synthesized. Different amounts of initial human genomic DNA were tested in the reaction, using genomic DNA at different concentrations: 50, 75, 100 ng/µl.

The 20 µl Component A was set up by combining:
5 µl 10×HDA Buffer A
2 µl of Human genomic DNA (50 to 100 ng/µl)
2 µl of 10 µM primer-dnmt5 (5' GGAAGCTGCTAAGG ACTAGTT 3' (SEQ ID NO:14))
2 µl of 10 µM primer-dnmt3 (5' CCATGTACCACAC ATGTGAAC 3' (SEQ ID NO:15))
2 µl dNTPs (10 mM)
7 µl dH$_2$O Thirty µl of Component B was prepared by mixing:
5 µl 10×HDA Buffer B
3 µl 100 mM ATP
1 µl exo$^-$ Klenow Fragment (5 units/µl)
0.5 µl UvrD helicase (200 ng/µl)
0.5 µl MutL (800 ng/µl)
0.9 µl T4 gp32 (5 µg/µl)
19.1 µl dH$_2$O The reaction Component A was heated for 10 min at 95° C., 1 min at 53° C., and 2 min at 37° C. Component B was then added to the Component A after it cooled down to 37° C. The reaction was continued for two more hours at 37° C. and was then terminated by addition of 12.5 µl stop-buffer. Reaction products were analyzed on a 3% GPG LMP agarose gel (FIG. 6). A band of around 124 bp could be detected by ethidium bromide staining and its size was in agreement with the length of the target in the initial dnmt1 gene.

EXAMPLE VII

Amplification of a Target Sequence from an RNA Sample by HDA

In this Example, we disclose a method to amplify a target sequence from RNA samples. Rat total RNA was used as nucleic acid substrate and was first converted to a single stranded cDNA product using The ProtoScript Kit from New England Biolabs (Beverly, Mass.):

The reaction was set up by combining:
2 µl Rat total RNA (0.5 µg/µl)
2 µl primer dT$_{23}$VN (50 µM, New England Biolabs (Beverly, Mass.))
4 µl dNTP (2.5 mM)
8 µl H2O and was incubated at 70° C. 5 min, then kept on ice.

After that, the following reagents were then added to the reaction tube:
2 µl 10×RT buffer (New England Biolabs (Beverly, Mass.))
1 µl RNase inhibitor (10 u/µl)
1 µl M-MulV reverse transcriptase (25 u/µl)

The RT reaction was incubated at 42° C. for 1 hr, followed by 95° C. for 5 min. Two µl of the single-stranded cDNA product was added into Component A in HDA which was started by combining:
5 µl 10×HDA Buffer A
2 µl of first strand cDNA product
1 µl of 10 µM primer-sfo (5' ACCGCATCGAATGCATG TGGATCTCACCACCAACTGCTTAGC 3' (SEQ ID NO:16))
1 µl of 10 µM primer-sre (5' CGATTCCGCTCCAGACT-TGGAT CTGATGGCATGGACTGTGGT 3' (SEQ ID NO:17))
2 µl dNTPs (10 mM)
9 µl dH$_2$O Thirty µl of reaction Component B was prepared by mixing:
5 µl 10×HDA Buffer B
2 µl 100 mM ATP
1 µl exo$^-$ Klenow Fragment (5 units/µl)
0.5 µl UvrD helicase (200 ng/µl)
0.5 µl MutL (800 ng/µl)
0.9 µl T4 gp32 (5 µg/µl)
20.1 µl dH$_2$O The reaction Component A was heated for 2 min at 95° C., 1 min at 53° C., and 2 min at 37° C. Fresh-made Component B was then added to the Component A after it cooled down to 37° C. The reaction was continued for two more hours at 37° C. and was then terminated by addition of 12.5 µl stop-buffer. Amplification products were analyzed on a 3% GPG LMP gel (FIG. 7). A band of around 130 bp was observed in the agarose gel in agreement with the predicted size of 136 bp. The amplification product was purified from the agarose gel and sequenced. The sequence of amplification product matched the sequence of the initial target of the rat glyceraldehyde-3-phosphate-dehydrogenase (GAPDH) gene, confirming that the amplification was sequence specific.

EXAMPLE VIII

HDA can Amplify and Detect a Target Sequence from as Low as 10 Copies of Bacterial Genomic DNA To determine the amplification power of HDA, we performed HDA reactions with various amounts of *Treponema denticola* genomic DNA. Each reaction was carried out as detailed in Example V, except the amount of genomic DNA. The first tube contained 100 ng of *Treponema denticola* genomic DNA corresponding to about $10^7$ copies of the *Treponema denticola* genome, and 10-fold serial dilutions were carried out until 10 copies of *Treponema denticola* genome were reached.

The UvrD-based HDA reactions were performed using primer-58861 and primer-58862 in Example V. Reaction products were analyzed on a 3% GPG LMP agarose gel (FIG. 8). In general, the intensities of the 97-bp HDA products decrease as a function of decreasing initial copy number (FIG. 8). A reaction performed without addition of target shows a faint band in FIG. 8 probably due to contamination of reagents. It is extremely difficult to maintain reagents free of target DNA contamination on a scale of 10 molecules. However, the intensity is still significantly higher than the background even at about 10 copies of initial target, suggesting that HDA is capable of amplifying single copy target sequence. With 10 copies of initial target, about 10 ng products were generated by HDA, which corresponds to $10^{10}$ molecules of 97-bp fragment. Thus the HDA method disclosed here is capable of achieving over a one billion-fold amplification.

EXAMPLE IX

Amplification of a Target Sequence from Bacterial Genomic DNA by HDA Without Heat Denaturation Most of the isothermal target amplification methods start with a heat denaturation step so that sequence-specific primers can anneal to the target sequence. Circumvention of the heat-denaturation step simplifies the amplification procedure. Accordingly, the UvrD-based HDA reaction was carried out at 37° C. without the initial denaturation/annealing step. The HDA reaction Component A was set up by combining the following reagents in one tube:

5 µl 10×HDA Buffer A
2 µl of *Treponema denticola* genomic DNA (50 ng/µl)
2 µl of 10 µM primer-58861 (5' CCAAATGATGCTTATG TTGCTT 3' (SEQ ID NO:11)
2 µl of 10 µM primer-58862 (5' CATAAGCCTCTCTT GGATCT 3' (SEQ ID NO:12))
2 µl dNTPs (10 mM)
5 µl 10×HDA Buffer B
3 µl 100 mM ATP
0.9 µl exo⁻ Klenow Fragment (5 units/µl)
0.5 µl UvrD helicase (200 ng/µl)
0.5 µl MutL (800 ng/µl)
0.9 µl T4 gp32 (5 µg/µl)
26.2 µl dH₂O and the 50 µl reaction was then incubated for two hours at 37° C. The reaction was then terminated by addition of 12.5 µl stop-buffer. Amplification products were analyzed on a 3% GPG LMP agarose gel (FIG. 9). The size of the amplification product matches the predicted size of the target DNA (97 bp).

EXAMPLE X

Method of Amplification of Long Target Sequences by HDA Using Replicative Helicase (T7 Gene 4 Helicase)

To test whether a hexameric replicative helicase, such as T7 Gp4B helicase, can be used to amplify a longer target sequence and to test whether different HDA systems can be used to perform HDA reaction, the T7 Gp4B helicase preparation was used along with the T7 Sequenase (USB, (Cleveland, Ohio)) to amplify a 2.3-kb target sequence. This target sequence was the *E. coli* Rep gene (GenBank Accession No. U00096), which was cloned into plasmid pCR2.1 (Invitrogen Corporation) and the resulting recombinant plasmid was named pCR-Rep. Primer 1224 and primer 1233, flanking the insertion site, were used to amplify the 2.3-kb target. A 50 µl HDA reaction was set up using two reaction Components, A and B, described below and mixing them in a sequential order. Two acetate-based reaction buffers were pre-made: 10×HDA Buffer A contains 350 mM Tris-Acetate (pH7.5) and 100 mM DTT; 10×HDA Buffer B contains 10 mM Tris-Acetate (pH7.5), 1 mg/ml BSA, and 100 mM Magnesium Acetate. Three parallel tubes were set up each contained 20 µl of reaction Component A by mixing the following Components in each tube:

5 µl 10×HDA Buffer A
1 µl of plasmid pCR-Rep (50 ng/µl)
1 µl of 10 µM primer-1224
1 µl of 10 µM primer-1233
3 µl dNTPs (10 mM)
9 µl dH₂O Three parallel tubes were prepared each contained 30 µl of reaction Component B by mixing the following Components in each tube:

5 µl 10×HDA Buffer B
9.3 µl Helicase preparation*
1 µl T7 Sequenase (1 u/µl, USB Corporation)
14.7 µl dH₂O

*Three different helicase preparations were used in HDA reactions. The first one was a T7 helicase preparation which contained 4.5 µl T7 Gp4B helicase (70 ng/µl), 1.3 µl T7 Gp2.5 SSB (5 µg/µl), 1.5 µl of 100 mM dTTP, and 2 µl H₂O (FIG. 5, lane 1). The second helicase preparation comprised a plurality of two helicases and it contained 4.5 µl T7 Gp4B helicase (70 ng/µl), 0.5 µl *E. coli* UvrD helicase (200 ng/µl), 0.5 µl MutL (800 ng/µl), 1.3 µl T7 Gp2.5 SSB (5 µg/µl), 1.5 µl of 100 mM dTTP, and 1 µl of 100 mM ATP (FIG. 5, lane 2). The third one was a negative control which contained 1.3 µl T7 Gp2.5 SSB (5 µg/µl), 1.5 µl of 100 mM dTTP and 6.5 µl H₂O (FIG. 5, lane 3).

HDA reactions were started by heating three tubes, each containing identical 20-µl Component A, at 95° C. for 2 min to denature the template and then at 37° C. for 1 min to hybridize the primers. Three freshly made Component B mixtures, each containing a different helicase preparation, were then added to each of the Component A mixtures. The reaction continued for two more hours at 37° C. and was then terminated upon addition of 12.5 µl stop-buffer (1% SDS, 0.05 M EDTA, 30% glycerol, 0.2% Bromophenol blue). Amplification products were visualized on a 1% agarose gel in TBE buffer and ethidium bromide (FIG. 10). In the presence of T7 Gp4B helicase preparation, an amplification product around 2.3 kb was observed and it matched the predicted target size (FIG. 10, lane 1). In the presence of a helicase preparation comprised of T7 Gp4B helicase and E. coli UvrD helicase, a similar 2.3-kb product was observed (FIG. 10, lane 2). In addition, no amplification product was observed in the negative control, in which no helicase was present in the helicase preparation (FIG. 10, lane 3). The amplification products from lane 1 and lane 2 were later sequenced and the sequencing results confirmed that the products were derived from the Rep gene.

EXAMPLE XI

Method of Amplification of DNA Fragment by HDA Using RecBCD

A nuclease-deficient mutant RecB$^{D1067A}$CD (Wang et al., J. Biol. Chem. 275:507–513 (2000)) was used in a HDA reaction to amplify a 400-bp DNA fragment. This blunt-end dsDNA template was generated by a PCR reaction using a pUC19-derivative containing a 400-bp insert between primer-1224 and primer-1233 (New England Biolabs, Inc. (Beverly, Mass.)). The cloning and purification of the RecB$^{D1067A}$CD protein has been described previously (Wang et al., J. Biol. Chem. 275:507–513 (2000)). A 50-μl reaction was set up by combining the following reagents in one tube:

5 μl 10×HDA Buffer (360 mM Tris-Acetate (pH7.5), 250 mM KOAC, 100 mM DTT, 1 mg/ml BSA, and 50 mM Magnesium Acetate)
1 μl of 400-bp template (2 ng/μl)
1.5 μl of 10 μM primer-1224
1.5 μl of 10 μM primer-1233
2 μl dNTPs (10 mM)
2 μl 100 mM ATP
1 μl Sequenase Version 2.0 (1.3 unit/μl)
0.5 μl RecB$^{D1067A}$CD helicase (130 ng/μl)
1.3 μl T4 gp32 (3.8 μg/μl)
26.2 μl dH$_2$O The 50 μl reaction was incubated for one hour at 37° C. and then terminated by addition of 12.5 μl stop-buffer. Amplification products were analyzed on a 1% agarose gel (FIG. 11, lane 2). The size of the amplification product matches the predicted size of the target DNA (400 bp). A control reaction without RecB$^{D1067A}$CD helicase did not give a product (FIG. 11, lane 3).

EXAMPLE XII

Method of Thermostable Helicase-Dependant Amplification of a Specific Sequence

Performing HDA at high temperature using a thermostable helicase and a thermostable polymerase may increase the specificity of primer binding and improve the specificity of amplification. In this example, we disclose a method to amplify and detect a specific target sequence from a bacterial genome of an oral pathogen, *Treponema denticola* ATCC No. 35405, using the Tte-UvrD-based thermostable Helicase-Dependent Amplification or t-HDA system.

1. Obtaining a Thermostable Helicase

A thermostable UvrD-like helicase, Tte-UvrD, was cloned and purified from a completely sequenced thermostable bacterium, *Thermoanaerobacter tengcongensis* (Bao, et al., Genome Res. 12:689–700 (2000)). The nucleotide sequence of the UvrD gene of *T. tengcongensis*, which encodes the Tte-UvrD helicase, is located between positions 605,527 and 607,668 of the *T. tengcongensis* genome and the sequence can be found in GenBank (Accession No.: NC_003869; Bao, et al., Genome Res. 12:689–700 (2000)). PCR was used to amplify the Tte-UvrD gene using *T. tengcongensis* genomic DNA (100 ng) plus primer TUF (5'-ATACATAT-GATTGGAGTGAAAAAGATGAA-3' (SEQ ID NO:18)) and primer TUR (5'-AAATAAGCTCTTCAG CAA-GAAATTGCCTTAATAGGAG-3' (SEQ ID NO:19)). The primers contained restrictions enzymes sites that allowing the cloning of the Tte-UvrD gene into the NdeI and SapI sites of pTYB1 (New England Biolabs, Inc., (Beverly, Mass.)). PCR products was digested with NdeI and Sa$\mu$l and then was ligated to the digested pTYBI. Ligation products were transformed into ER2502 cells. Positive transformants were screened by selective growth on LB plates containing 100 μg/ml ampicillin, followed by colony PCR and sequencing of the insert. After analysis of sequencing results, correct constructs were transformed into *E. coli* ER2566 cells. ER2566 cells containing pTYB1-Tte-UvrD were grown at 37° C. in LB media supplemented with 100 ug/ml ampicillin. When OD$_{550}$ reached ~0.65, protein expression was induced with 0.4 mM IPTG. After an overnight incubation at 15° C., cells were harvested by centrifugation.

The chitin binding domain (CBD) of the intein tag allowed affinity purification of the fusion proteins on a chitin bead column (New England Biolabs, Inc., (Beverly, Mass.)). The Tte-UvrD helicase was first purified using a chitin column and the protocol is described in detail in Example I (UvrD and MutL purification). Next, Tte-UvrD was further purified by a 1-ml heparin TSK column (Pharmacia (Piscataway, N.J.)). Fractions containing Tte-UvrD were analyzed by SDS-PAGE. The pure fractions were pooled and dialyzed overnight against storage buffer (20 mM Tris-HCl (pH8.2), 200 mM NaCl, 1 mM EDTA, 1 mM EGTA, 15 mM 2-mercaptoethanol, 50% glycerol). The final concentration was determined using the Bradford protein assay (Bradford Anal. Biochem. 72:248–254 (1976)) and SDS-PAGE.

2. Thermostable Helicase-Dependent Amplification (t-HDA)

The purified thermostable Tte-UvrD helicase was used in along a thermostable Bst DNA polymerase large fragment (New England Biolabs, Inc., (Beverly, Mass.)) to selectively amplify a target sequence from genomic DNA at high temperature. A restriction endonuclease gene earIR was chosen as the target gene (FIG. 16 (SEQ ID NO:10)). Two primers, one for each end of the target fragment, were designed and they have high melting temperature (~75° C.) so that they can hybridize to the target sequence at high temperature. The reaction buffers and protocol were modified for genomic DNA amplification. Reaction buffer is 1033 ThermoPol reaction Buffer (New England Biolabs, Inc., (Beverly, Mass.)): 200 mM Tris-HCl (pH8.8), 100 mM KCl, 100 mM (NH$_4$)$_2$SO$_4$, 20 mM MgSO$_4$, 1% Triton X-100.

Thirty-five μl of Component A was made by combining:
3.5 μl 10× ThermoPol Buffer
2 μl of 0.83 pM *Treponema denticola* genomic DNA
1 μl of 10 μM primer p5-76 (5'-GGCCAGTTTGAA TAAGACAATGAATTATT-3' (SEQ ID NO:20))
1 μl of 10 μM primer p3-76 (5'-ATTTTGAAACACA AGAATGGAAATGTGAAAG-3'(SEQ ID NO:21))
2 μl dNTPs (10 mM)
1.5 μl dATP (100 mM)
24 μl dH$_2$O Fifteen μl of reaction Component B was prepared by mixing:

1.5 µl 10× ThermoPol Buffer
2.6 µl Bst DNA Polymerase, Large Fragment (8 units/µl)
1 µl UvrD-tte helicase (100 ng/µl)
0.9 µl T4 gp32 (5 µg/µl)
9 µl dH$_2$O The HDA reaction was started by heating Component A at 95° C. for 2 min to denature the template. The Component A was then cooled down to 60° C., kept at 60° C. for 3 min to anneal primers. Fifteen µl of freshly made Component B were added to 35 µl Component A following the denaturation and annealing steps. The reaction continued for one more hour at 60° C. and was then terminated upon addition of 12.5 µl stop-buffer (1% SDS, 0.05 M EDTA, 30% glycerol, 0.2% Bromophenol blue). Amplification products were visualized on a 2% GPG LMP agarose gel in TBE buffer and ethidium bromide. The size of the amplified DNA matches the predicated target size of 82 bp (FIG. 12).

EXAMPLE XIII

Method of Amplification and Detection of a Specific Sequence from Neisseria Gonorrhoeae by t-HDA In this Example, we disclose a method to amplify and detect a specific target sequence from a different bacterial genome, *Neisseria gonorrhoeae*. *N. gonorrhoeae* is a human pathogen which causes gonorrhea, one of the most common sexually transmitted diseases. *N. gonorrhoeae* genomic DNA was purchased from American Type Culture Collection (ATCC No. 700825, (Manassas, Va.)). Two primers, one for each end of the target sequence (CATATGTAACAG-CAGGTCAGGCCATATCCA ATATTCCACAAAATGC-CAGTAATAATGAATTACTGAAAATCAGCGATA AAA-CACGCCGTATGTTG (SEQ ID NO:22)), were synthesized and they have a melting temperature of ~78° C. The reaction buffers and protocol were modified for genomic DNA amplification. Reaction buffer is 10× ThermoPol reaction Buffer (New England Biolabs, Inc., (Beverly, Mass.)).

Thirty-five µl of Component A was made by combining:
3.5 µl 10× ThermoPol Buffer
2 µl of *N. gonorrhoeae* genomic DNA (50 ng/µl)
1 µl of 10 µM primer H153 (5'-CATATGTAACAG-CAGGT CAGGCCATAT-3' (SEQ ID NO:23)
1 µl of 10 µM primer H154 (5'-CAACATACGGCGT GTTTTATCGCTGAT -3' (SEQ ID NO:24)
2 µl dNTPs (10 mM)
1.5 µl dATP (100 mM)
24 µl dH$_2$O Fifteen µl of reaction Component B was prepared by mixing:
1.5 µl 10× ThermoPol Buffer
2.6 µl Bst DNA Polymerase, Large Fragment (8 units/µl)
1 µl UvrD-tte helicase (100 ng/µl)
0.9 µl T4 gp32 (5 µg/µl)
9 µl dH$_2$O The HDA reaction was started by heating Component A at 95° C. for 2 min to denature the template. The Component A was then cooled down to 60° C., kept at 60° C. for 3 min to anneal primers. Fifteen µl of freshly made Component B was added to 35 µl Component A following the denaturation and annealing steps. The reaction continued for one more hour at 60° C. and was then terminated upon addition of 12.5 µl stop-buffer (1% SDS, 0.05 M EDTA, 30% glycerol, 0.2% Bromophenol blue). Amplification products were visualized on a 2% GPG LMP agarose gel in TBE buffer and ethidium bromide. In the presence of the Tte-UvrD helicase, Gp32 SSB, and the large fragment of Bst DNA polymerase, a dominant band around 95-bp was observed on the gel and it matches the predicated target size (FIG. 13, lane 1). Gp32 SSB was eliminated in a parallel reaction and the 95-bp product was also observed (FIG. 13, lane 2), suggesting that single-stranded DNA binding protein is not required for this HDA system. When the Tte-UvrD helicase is absent from the reaction, no amplification is observed (FIG. 13, lane 3), which further confirms that this is a helicase-dependent amplification. This example demonstrates that HDA requires a minimal of two enzymatic activities, a DNA helicase activity and a DNA polymerase activity.

EXAMPLE XIV

Real Time Detection of a Target Sequence of Pathogenic Bacteria in a Sample

HDA can be combined with other technologies and can be used for genome typing such as determining single nucleotide polymorphisms (SNP) and for the identification of infectious agents. For example, HDA can be coupled with other nucleic acid detection methods, such as fluorescent-labeled LUX™ Primers (Invitrogen Corporation, Carlsbad, Calif.) and a real-time fluorescent detection system (iCycler, Bio-Rad Laboratories Inc., Hercules, Calif.), to amplify and detect the presence of a target sequence in real time. This example illustrates real-time amplification and detection of a target sequence (FIG. 16 (SEQ ID NO:10)) in a bacterial pathogen, *Treponema denticola* (ATCC No. 35405), using HDA method and the UvrD HDA system. The fluorescent-labeled primer, primer-175-LUX (5' cacatttTGAAACA-CAAGAATGGAAATGTG 3' (SEQ ID NO:25)), was customer designed based on the target sequence (FIG. 16 (SEQ ID NO:10)) and obtained from Invitrogen Corporation. The reaction buffers were pre-made: 10×HDA Buffer A contains 350 mM Tris-Acetate (pH7.5) and 100 mM DTT. 10×HDA Buffer B contains 10 mM Tris-Acetate (pH7.5), 1 mg/ml BSA, and 100 mM Magnesium Acetate.

To test the reproducibility of real-time HDA reaction, two parallel reactions were carried out (FIG. 12, line 1 and line 2). Each reaction was set up as following: 20 µl Component A was made by combining:
5 µl 10×HDA Buffer A
1 µl of *Treponema denticola* genomic DNA (30 ng/µl)
2 µl of 10 µM primer-175-LUX (5' cacatttTGAAACA-CAAG AATGGAAATGTG 3' (SEQ ID NO:25))
2 µl of 10 µM primer-175-Rev (5' GGCCAGTTTGAAT AAGACAATG 3' (SEQ ID NO:26))
2 µl of 10 mM dNTPs
8 µl dH$_2$O Thirty µl of reaction Component B was prepared by mixing:
5 µl 10×HDA Buffer B
1.5 µl 100 mM ATP
1 µl exo⁻ Klenow Fragment (5 units/µl)
0.5 µl UvrD helicase (200 ng/µl)
0.8 µl MutL (800 ng/µl)
1.2 µl T4 gp32 (5 µg/µl)
20 µdH$_2$O The reaction Component A was incubated for 2 min at 95° C. and then 1 min at 37° C. The freshly made Component B was then added to Component A after it cooled down to 37° C. The reaction was continued in an iCycler (Bio-Rad) at 37° C. The amplification product was detected in real-time by measuring fluorescent signals (490 nM for FAM) at a 5-min interval using a real-time PCR machine, iCycler (Bio-Rad). Fluorescent signals from reactions 1 and 2 started to increase at 40 minutes and crossed $T_t$ (time of threshold) line around 50 minutes (FIG. 14, lines 1 and 2). The $T_t$ value for these two reactions were about 50 minutes. In addition, the curves derived from reaction 1 and reaction 2 were very similar, suggesting the reproducibility of real-time HDA reaction was good. In the negative control, fluorescent signal remained below $T_t$ line (FIG. 14, line 3).

What is claimed is:

1. A method for exponentially and selectively amplifying a target nucleic acid in a helicase-dependent reaction, the method comprising:
   (a) providing single strand templates of the target nucleic acid to be amplified;
   (b) adding oligonucleotide primers for hybridizing to the templates of step (a);
   (c) synthesizing an extension product of the oligonucleotide primers which are complementary to the templates, by means of a DNA polymerase to form a duplex;
   (d) contacting the duplex of step (c) with a helicase preparation for unwinding the duplex such that the helicase preparation comprises a helicase and a single strand binding protein (SSB) unless the helicase preparation comprises a thermostable helicase wherein the single strand binding protein is optional; and
   (e) repeating steps (b)–(d) to exponentially and selectively amplify the target nucleic acid in a helicase-dependent reaction such that amplification does not occur in the absence of the helicase as determined by gel electrophoresis.

2. A method according to claim 1, wherein amplification is isothermal.

3. A method according to claim 1, wherein the target nucleic acid is a DNA.

4. A method according to claim 1, wherein the target nucleic acid is an RNA.

5. A method according to claim 1, wherein the target nucleic acid is a double-stranded nucleic acid, the double-stranded nucleic having been denatured by heat or enzymatically prior to step(a).

6. A method according to claim 1, wherein the target nucleic acid has a size in the range of about 50 bp to 100 kb.

7. A method of claim 1, wherein the oligonucleotide primers are a pair of oligonucleotide primers wherein one primer hybridizes to 5'-end and one primer hybridizes to 3'-end of the target nucleic acid to be selectively amplified.

43

8. A method according to claim 1, wherein the oligonucleotide primers have a length and a GC content so that the melting temperature of the oligonucleotide primers is about 10° C.–30° C. above the reaction temperature of hybridization during amplification.

9. A method according to claim 8, wherein the DNA polymerase is selected from a Klenow fragment of E. coli DNA polymerase I, T7 DNA polymerase (Sequenase) and Bst polymerase large fragment.

10. A method according to claim 9, wherein the DNA polymerase lacks 5' to 3' exonuclease activity.

11. A method according to claim 10, wherein the DNA polymerase possesses strand displacement activity.

12. A method according to claim 1, wherein the helicase preparation comprises a single helicase.

13. A method according to claim 1, wherein the helicase preparation comprises a plurality of helicases.

14. A method according to claim 1, wherein the helicase preparation comprises a 3' to 5' helicase.

15. A method according to claim 1, wherein the helicase preparation comprises a 5' to 3' helicase.

16. A method according to claim 1, wherein the helicase preparation comprises a superfamily 1 helicase.

17. A method according to claim 1, wherein the helicase preparation comprises a superfamily 4 helicase.

18. A method according to claim 1, wherein the helicase preparation is selected from a superfamily 2 helicase, a superfamily 3 helicase, and an AAA$^+$ helicase.

19. A method according to claim 1, wherein the helicase preparation comprises a hexameric helicase.

20. A method according to claim 1, wherein the helicase preparation comprises a monomeric or dimeric helicase.

21. A method according to claim 1, wherein the helicase preparation comprises a UvrD helicase or homolog thereof.

22. A method according to claim 21, wherein the UvrD helicase comprises a thermostable helicase or homolog thereof.

23. A method according to claim 1, wherein the helicase preparation comprises one or more helicases selected from the group consisting of: a UVrD helicase, a recBCD helicase, E. coli UvrD helicase, Tte-UvrD helicase, T7 Gp4 helicase, RecBCD helicase, DnaB helicase, MCM helicase, Rep helicase, RecQ helicase, PcrA helicase, SV40 large T antigen helicase, Herpes virus helicase, yeast Sgs1 helicase, DEAH_ATP-dependent helicases and Papillomavirus helicase E1 protein and homologs thereof.

24. A method according to claim 21, wherein the UvrD helicase is E.coli UvrD helicase.

25. A method according to claim 22, wherein the thermostable helicase is Tte-UvrD helicase.

26. A method according to claim 1, wherein the helicase preparation comprises a RecBCD helicase.

27. A method according to claim 13, wherein the helicase preparation comprises T7 gene 4 helicase and E. coli UvrD helicase.

28. A method according to claim 1, wherein the energy source in the helicase preparation is selected from adenosine triphosphate (ATP), deoxythymidine triphosphate (dTTP) or deoxyadenosine triphosphate (dATP).

29. A method of claim 28, wherein the ATP, dATP or dTTP are at a concentration in the range of about 0.1–50 mM.

30. A method according to claim 1, wherein the helicase preparation comprises a single strand binding protein.

31. A method according to claim 30, wherein the single stranded binding protein (SSB) is selected from T4 gene 32 SSB, E.coli SSB, T7 gene 2.5 SSB, phage phi29 SSB and derivatives therefrom.

44

32. A method according to claim 1, wherein the helicase preparation comprises an accessory protein.

33. A method according to claim 32, wherein the accessory protein for a UvrD helicase is MutL.

34. A method according to claim 1, wherein the helicase preparation comprises E. coli UvrD helicase, ATP, E. coli MutL protein and T4Gp32.

35. A method according to claim 1, wherein the helicase preparation comprises E.coli RecBCD, ATP, and T4 Gp32 SSB.

36. A method according to claim 1, wherein the helicase preparation comprises T7 Gp4B helicase, dTTP, and T7 Gp2.5 SSB.

37. A method according to claim 1, wherein the helicase preparation comprises the thermostable Tte-UvrD helicase, dATP or ATP.

38. A method according to claim 1, wherein the helicase preparation comprises the thermostable Tte-UvrD helicase, dATP or ATP and T4 gp32 SSB.

39. A method according to claim 1, wherein steps (b)–(e) are performed at a substantially single temperature in the range of about 20° C.–75° C.

40. A method according to claim 1, wherein steps (b)–(e) are performed at about 37° C.

41. A method according to claim 22, wherein steps (b)–(e) are performed at about 60° C. and the helicase in the helicase preparation is a thermostable helicase.

42. A method according to claim 1, wherein the target nucleic acid is obtained from a pathogen in a biological sample, and step (e) further comprises amplifying the target nucleic acid to detect the pathogen.

43. A method according to claim 1, wherein the target DNA is chromosomal DNA and step (e) further comprises detecting a sequence variation in the chromosomal DNA.

44. A method according to claim 43, wherein the sequence variation is a single nucleotide polymorphism.

45. A method for determining whether a helicase is suited for exponentially and selectively amplifying a target nucleic acid in a helicase-dependent reaction, comprising;

(a) preparing a helicase preparation comprising the helicase, an NTP or dNTP, a buffer, wherein the buffer has a pH in the range of about pH 6.0–9.0, a concentration of NaCl or KCl in a concentration range of 0–200 mM, and Tris-acetate or Tris-HCl and an accessory protein to which is added one or more single strand binding proteins unless the helicase is thermostable wherein the single strand binding protein is not required;

(b) adding a target nucleic acid, oligonucleotide primers, four dNTPs and a DNA polymerase to the helicase preparation;

(c) incubating the mixture at a temperature between about 20° C. and 75° C.; and (d) analyzing the DNA on an agarose gel to determine whether selective and exponential amplification has occurred.

46. A method according to claim 45, further comprising optimizing the conditions of helicase dependent amplification by varying the concentration of any or each of: the helicase; the single stranded binding protein; the accessory protein; the NTP or dNTP; the salt concentration; the pH; and varying the buffer type; the temperature; the time of incubation and the length of the target nucleic acid.

47. A method for helicase-dependent amplification of a target nucleic acid, comprising:

(a) adding to the target nucleic acid, a helicase preparation comprising a helicase and a single strand binding protein unless the helicase is a thermostable helicase in which case the single strand binding protein is not required, a plurality of oligonucleotide primers and one or more polymerases; and (b) amplifying, by helicase-dependent amplification, the target nucleic acid wherein the amplification does not occur in the absence of the helicase as determined by gel electrophoresis.

* * * * *

UNITED STATES PATENT AND TRADEMARK OFFICE
CERTIFICATE OF CORRECTION

| | | |
|---|---|---|
| PATENT NO. | : 7,282,328 B2 | Page 1 of 1 |
| APPLICATION NO. | : 10/665633 | |
| DATED | : October 16, 2007 | |
| INVENTOR(S) | : Huimin Kong et al. | |

It is certified that error appears in the above-identified patent and that said Letters Patent is hereby corrected as shown below:

At column 19, line number 60, delete "manufactory" and insert -- manufacturer --, therefor.

At column 24, line number 29, delete "H2O" and insert -- $H_2O$ --, therefor.

At column 24, line number 36, delete "M-MulV" and insert -- M-MuLV --, therefor.

At column 42, claim number 5, line number 59, delete "nucleic" and insert -- nucleic acid --, therefor.

Signed and Sealed this
Tenth Day of May, 2011

David J. Kappos
*Director of the United States Patent and Trademark Office*

SEQUENCE LISTING

<160> NUMBER OF SEQ ID NOS: 26

<210> SEQ ID NO 1
<211> LENGTH: 30
<212> TYPE: DNA
<213> ORGANISM: Unknown
<220> FEATURE:
<223> OTHER INFORMATION: Primer 5A

<400> SEQUENCE: 1
ggtggtacca tggacgtttc ttacctgctc                                     30

<210> SEQ ID NO 2
<211> LENGTH: 35
<212> TYPE: DNA
<213> ORGANISM: unknown
<220> FEATURE:
<223> OTHER INFORMATION: primer 3A

<400> SEQUENCE: 2
ggtggtgctc ttccgcacac cgactccagc cgggc                               35

<210> SEQ ID NO 3
<211> LENGTH: 30
<212> TYPE: DNA
<213> ORGANISM: unknown
<220> FEATURE:
<223> OTHER INFORMATION: primer 5B

<400> SEQUENCE: 3
ggtggtcata tgccaattca ggtcttaccg                                     30

<210> SEQ ID NO 4
<211> LENGTH: 40
<212> TYPE: DNA
<213> ORGANISM: unknown
<220> FEATURE:
<223> OTHER INFORMATION: primer 3B

<400> SEQUENCE: 4
ggtggttgct cttccgcact catctttcag ggcttttatc                          40

<210> SEQ ID NO 5
<211> LENGTH: 70
<212> TYPE: DNA
<213> ORGANISM: unknown
<220> FEATURE:
<223> OTHER INFORMATION: top oligonucleotides

<400> SEQUENCE: 5
tggctggtca ccagagggtg gcgcggaccg agtgcgctcg gcggctgcgg agagggtag     60 agcaggcagc                                                           70

<210> SEQ ID NO 6
<211> LENGTH: 70
<212> TYPE: DNA
<213> ORGANISM: unknown
<220> FEATURE:
<223> OTHER INFORMATION: bottom oligonucleotide

```
<400> SEQUENCE: 6
gctgcctgct ctacccctct ccgcagccgc cgagcgcact cggtccgcgc caccctctgg      60
tgaccagcca                                                             70

<210> SEQ ID NO 7
<211> LENGTH: 43
<212> TYPE: DNA
<213> ORGANISM: unknown
<220> FEATURE:
<223> OTHER INFORMATION: 5' primer

<400> SEQUENCE: 7
catgttaggt tctatggatc gagtctggct ggtcaccaga ggg                        43

<210> SEQ ID NO 8
<211> LENGTH: 45
<212> TYPE: DNA
<213> ORGANISM: unknown
<220> FEATURE:
<223> OTHER INFORMATION: 3' primer

<400> SEQUENCE: 8
tcccttagag gtcacattgg atcgagtcgc tgcctgctct acccc                      45

<210> SEQ ID NO 9
<211> LENGTH: 2647
<212> TYPE: DNA
<213> ORGANISM: unknown
<220> FEATURE:
<223> OTHER INFORMATION: plasmid pAH1

<400> SEQUENCE: 9
tcgcgcgttt cggtgatgac ggtgaaaacc tctgacacat gcagctcccg gagacggtca      60
cagcttgtct gtaagcggat gccgggagca gacaagcccg tcaggcgcg tcagcgggtg     120 ttggcgggtg tcgggctgg cttaactatg cggcatcaga gcagattgta ctgagagtgc     180
accatatgcg gtgtgaaata ccgcacagat gcgtaaggag aaaataccgc atcaggcgcc    240
attcgccatt caggctgcgc aactgttggg aagggcgatc ggtgcgggcc tcttcgctat    300
tacgccagct ggcgaaaggg ggatgtgctg caaggcgatt aagttgggta acgccagggt    360
tttcccagtc acgacgttgt aaaacgacgg ccagtgaatt gcatgctcag cttggcgtaa    420
tcatggtcat agctgtttcc tgtgtgaaat tgttatccgc tcacaattcc acacaacata    480
cgagccggaa gcataaagtg taaagcctgg ggtgcctaat gagtgagcta actcacatta    540
attgcgttgc gctcactgcc cgctttccag tcgggaaacc tgtcgtgcca gctgcattaa    600
tgaatcggcc aacgcgcggg gagaggcggt ttgcgtattg ggcgctcttc cgcttcctcg    660
ctcactgact cgctgcgctc ggtcgttcgg ctgcggcgag cggtatcagc tcactcaaag    720
gcggtaatac ggttatccac agaatcaggg gataacgcag gaaagaacat gtgagcaaaa    780
ggccagcaaa aggccaggaa ccgtaaaaag gccgcgttgc tggcgttttt ccataggctc    840 cgccccctg acgagcatca caaaaatcga cgctcaagtc agaggtggcg aaacccgaca     900
ggactataaa gataccaggc gtttccccct ggaagctccc tcgtgcgctc tcctgttccg     960
accctgccgc ttaccggata cctgtccgcc tttctccctt cgggaagcgt ggcgctttct   1020
catagctcac gctgtaggta tctcagttcg gtgtaggtcg ttcgctccaa gctgggctgt   1080
gtgcacgaac cccccgttca gcccgaccgc tgcgccttat ccggtaacta tcgtcttgag   1140
```

```
tccaacccgg taagacacga cttatcgcca ctggcagcag ccactggtaa caggattagc    1200
agagcgaggt atgtaggcgg tgctacagag ttcttgaagt ggtggcctaa ctacggctac    1260
actagaagga cagtatttgg tatctgcgct ctgctgaagc cagttacctt cggaaaaaga    1320
gttggtagct cttgatccgg caaacaaacc accgctggta cggtggtttt ttttgtttgc    1380
aagcagcaga ttacgcgcag aaaaaaagga tctcaagaag atcctttgat cttttctacg    1440
gggtctgacg ctcagtggaa cgaaaactca cgttaaggga ttttggtcat gagattatca    1500
aaaaggatct tcacctagat ccttttaaat taaaaatgaa gttttaaatc aatctaaagt    1560
atatatgagt aaacttggtc tgacagttac caatgcttaa tcagtgaggc acctatctca    1620
gcgatctgtc tatttcgttc atccatagtt gcctgactcc ccgtcgtgta gataactacg    1680
atacgggagg gcttaccatc tggccccagt gctgcaatga taccgcgaga cccacgctca    1740
ccggctccag atttatcagc aataaaccag ccagccggaa gggccgagcg cagaagtggt    1800
cctgcaactt tatccgcctc catccagtct attaattgtt gccgggaagc tagagtaagt    1860
agttcgccag ttaatagttt gcgcaacgtt gttgccattg ctacaggcat cgtggtgtca    1920
cgctcgtcgt ttggtatggc ttcattcagc tccggttccc aacgatcaag gcgagttaca    1980
tgatccccca tgttgtgcaa aaaagcggtt agctccttcg gtcctccgat cgttgtcaga    2040
agtaagttgg ccgcagtgtt atcactcatg gttatggcag cactgcataa ttctcttact    2100
gtcatgccat ccgtaagatg cttttctgtg actggtgagt actcaaccaa gtcattctga    2160
gaatagtgta tgcggcgacc gagttgctct tgcccggcgt caatacggga taataccgcg    2220
ccacatagca gaactttaaa agtgctcatc attggaaaac gttcttcggg gcgaaaactc    2280
tcaaggatct taccgctgtt gagatccagt tcgatgtaac ccactcgtgc acccaactga    2340
tcttcagcat cttttacttt caccagcgtt ctgggtgagc aaaaacagg aaggcaaaat    2400 gccgcaaaaa agggaataag ggcgacacgg aaatgttgaa tactcatact cttccttttt    2460
caatattatt gaagcattta tcagggttat tgtctcatga gcggatacat atttgaatgt    2520
atttagaaaa ataaacaaat aggggttccg cgcacatttc cccgaaaagt gccacctgac    2580
gtctaagaaa ccattattat catgacatta acctataaaa ataggcgtat cacgaggccc    2640
tttcgtc                                                              2647
```

<210> SEQ ID NO 10
<211> LENGTH: 993
<212> TYPE: DNA
<213> ORGANISM: unknown
<220> FEATURE:
<223> OTHER INFORMATION: earRI gene of T. dentcola

<400> SEQUENCE: 10

```
atgagtaggc gtgaagtaaa aaatcaaaca aatatttcta gaattgaagg aattaaacca     60
aatgatgctt atgttgctta tgtatgtgta caatgtaaca atttgaatat gataaatatt    120
ggacaaaaat tattagatcc aagagaggct tatgaaacac aagaatggaa atgtgaaaga    180
tgtggatttt tacatagtaa aaataattca ttgtcttatt caaactggcc agaagaaagt    240
aaaaagaaag gttctattcc tgtacaaaga ttttggcaag cttttttttag agtatataca    300 gagaataaag aagcatattg gaaacaatgt aattgttgtg gaaaaatatt accattttcc    360
gcatttagca agcatattgg ttttggccct cttgaaagac aaatggaatg tagagcttgt    420
aagggagtga taaatgcatt tttaaatcca gaaagaacag aagatcaatt aagagagtca    480
aatgttagga gacgtgttgc cgatttgttt gttaaaaaag aaaataaatc taaagatgat    540
```

```
ggatttatta aagatttatt taaacgtttt ggttcaaagt gctttaaaac aaagaaatat      600
ctaaatattc atgatagaaa ttcttgggct atagatcata ttttaccatc aaaatatctt      660
tatcctctta caaagaaaa tgctgcacta ttatctgtag aagctaattc aataaaaga        720 gatcgttggc cttcagaatt ttatacaaat aatgaattaa tagaacttgc tacaataaca     780
ggagctgatt tacaattatt atcaaataaa acacctatta taaatccaaa tcttactgat     840
gaggatataa atgcaggtat tgagaattat ttgtctgttc gtgaaaattc aaaccttgag     900
aagcgagtag ctgaaataaa aaaaatcata atagactatc aattaacgga taaattatcg     960
aaaagcaaca agaatttact tggtttatct taa                                  993
```

```
<210> SEQ ID NO 11
<211> LENGTH: 22
<212> TYPE: DNA
<213> ORGANISM: unknown
<220> FEATURE:
<223> OTHER INFORMATION: primer 58861

<400> SEQUENCE: 11
ccaaatgatg cttatgttgc tt                                               22

<210> SEQ ID NO 12
<211> LENGTH: 20
<212> TYPE: DNA
<213> ORGANISM: unknown
<220> FEATURE:
<223> OTHER INFORMATION: primer 58862

<400> SEQUENCE: 12
cataagcctc tcttggatct                                                  20

<210> SEQ ID NO 13
<211> LENGTH: 22
<212> TYPE: DNA
<213> ORGANISM: unknown
<220> FEATURE:
<223> OTHER INFORMATION: primer 58863

<400> SEQUENCE: 13
tccacatctt tcacatttcc at                                               22

<210> SEQ ID NO 14
<211> LENGTH: 21
<212> TYPE: DNA
<213> ORGANISM: unknown
<220> FEATURE:
<223> OTHER INFORMATION: primer-dnmt5

<400> SEQUENCE: 14
ggaagctgct aaggactagt t                                                21

<210> SEQ ID NO 15
<211> LENGTH: 21
<212> TYPE: DNA
<213> ORGANISM: unknown
<220> FEATURE:
<223> OTHER INFORMATION: primer-dnmt3

<400> SEQUENCE: 15
ccatgtacca cacatgtgaa c                                                21

<210> SEQ ID NO 16
```

```
<211> LENGTH: 42
<212> TYPE: DNA
<213> ORGANISM: unknown
<220> FEATURE:
<223> OTHER INFORMATION: primer-sfo

<400> SEQUENCE: 16
accgcatcga atgcatgtgg atctcaccac caactgctta gc                    42

<210> SEQ ID NO 17
<211> LENGTH: 42
<212> TYPE: DNA
<213> ORGANISM: unknown
<220> FEATURE:
<223> OTHER INFORMATION: primer-sre

<400> SEQUENCE: 17
cgattccgct ccagacttgg atctgatggc atggactgtg gt                    42

<210> SEQ ID NO 18
<211> LENGTH: 29
<212> TYPE: DNA
<213> ORGANISM: unknown
<220> FEATURE:
<223> OTHER INFORMATION: primer TUF

<400> SEQUENCE: 18
atacatatga ttggagtgaa aaagatgaa                                   29

<210> SEQ ID NO 19
<211> LENGTH: 37
<212> TYPE: DNA
<213> ORGANISM: unknown
<220> FEATURE:
<223> OTHER INFORMATION: primer TUR

<400> SEQUENCE: 19
aaataagctc ttcagcaaga aattgcctta ataggag                          37

<210> SEQ ID NO 20
<211> LENGTH: 29
<212> TYPE: DNA
<213> ORGANISM: unknown
<220> FEATURE:
<223> OTHER INFORMATION: primer p5-76

<400> SEQUENCE: 20
ggccagtttg aataagacaa tgaattatt                                   29

<210> SEQ ID NO 21
<211> LENGTH: 31
<212> TYPE: DNA
<213> ORGANISM: unknown
<220> FEATURE:
<223> OTHER INFORMATION: primer p3-76

<400> SEQUENCE: 21
attttgaaac acaagaatgg aaatgtgaaa g                                31

<210> SEQ ID NO 22
<211> LENGTH: 95
<212> TYPE: DNA
<213> ORGANISM: unknown
<220> FEATURE:
<223> OTHER INFORMATION: N. gonorrhoeae specif target sequence

<400> SEQUENCE: 22
```

```
catatgtaac agcaggtcag gccatatcca atattccaca aaatgccagt aataatgaat      60
tactgaaaat cagcgataaa acacgccgta tgttg                                 95

<210> SEQ ID NO 23
<211> LENGTH: 27
<212> TYPE: DNA
<213> ORGANISM: unknown
<220> FEATURE:
<223> OTHER INFORMATION: primer H153

<400> SEQUENCE: 23
catatgtaac agcaggtcag gccatat                                          27

<210> SEQ ID NO 24
<211> LENGTH: 27
<212> TYPE: DNA
<213> ORGANISM: unknown
<220> FEATURE:
<223> OTHER INFORMATION: primer H154

<400> SEQUENCE: 24
caacatacgg cgtgttttat cgctgat                                          27

<210> SEQ ID NO 25
<211> LENGTH: 30
<212> TYPE: DNA
<213> ORGANISM: unknown
<220> FEATURE:
<223> OTHER INFORMATION: primer-175-LUX

<400> SEQUENCE: 25
cacattttga aacacaagaa tggaaatgtg                                       30

<210> SEQ ID NO 26
<211> LENGTH: 22
<212> TYPE: DNA
<213> ORGANISM: unknown
<220> FEATURE:
<223> OTHER INFORMATION: primer-175-Rev

<400> SEQUENCE: 26
ggccagtttg aataagacaa tg                                               22
```